(12) United States Patent
Delattre et al.

(10) Patent No.: US 10,351,838 B2
(45) Date of Patent: Jul. 16, 2019

(54) USE OF IDE AS A BIOMARKER FOR A SCALP CONDITION

(75) Inventors: Caroline Delattre, Vemars (FR);
Philemon Sirven, Poissy (FR);
Dominique Bernard, Vanves (FR)

(73) Assignee: L'OREAL, Paris (FR)

( * ) Notice: Subject to any disclaimer, the term of this patent is extended or adjusted under 35 U.S.C. 154(b) by 54 days.

(21) Appl. No.: 13/993,907

(22) PCT Filed: Dec. 12, 2011

(86) PCT No.: PCT/IB2011/055600
§ 371 (c)(1),
(2), (4) Date: Sep. 4, 2013

(87) PCT Pub. No.: WO2012/080929
PCT Pub. Date: Jun. 21, 2012

(65) Prior Publication Data
US 2013/0337085 A1  Dec. 19, 2013

Related U.S. Application Data

(60) Provisional application No. 61/457,083, filed on Dec. 23, 2010.

(30) Foreign Application Priority Data

Dec. 13, 2010 (FR) .................................. 10 60429

(51) Int. Cl.
| | | |
|---|---|---|
| *C12Q 1/37* | (2006.01) | |
| *C12N 9/64* | (2006.01) | |
| *C07K 7/06* | (2006.01) | |
| *C07K 7/08* | (2006.01) | |
| *G01N 33/68* | (2006.01) | |
| *C12Q 1/34* | (2006.01) | |

(52) U.S. Cl.
CPC .............. *C12N 9/6489* (2013.01); *C07K 7/06* (2013.01); *C07K 7/08* (2013.01); *C12Q 1/34* (2013.01); *G01N 33/6893* (2013.01); *G01N 2333/96486* (2013.01); *G01N 2800/20* (2013.01)

(58) Field of Classification Search
None
See application file for complete search history.

(56) References Cited

U.S. PATENT DOCUMENTS

| | | | | | |
|---|---|---|---|---|---|
| 4,053,630 | A | * | 10/1977 | Yu et al. ...................... | 514/502 |
| 4,166,845 | A | * | 9/1979 | Hansen et al. ............... | 514/401 |
| 2003/0036174 | A1 | * | 2/2003 | Kim et al. .................... | 435/69.4 |
| 2003/0175803 | A1 | * | 9/2003 | Tsionsky ............... | C12Q 1/485 435/7.1 |
| 2004/0253194 | A1 | * | 12/2004 | Rioux et al. ............... | 424/70.11 |
| 2005/0124690 | A1 | * | 6/2005 | Yoon et al. ................... | 514/462 |
| 2008/0206230 | A1 | * | 8/2008 | Rougeot et al. ........... | 424/130.1 |
| 2009/0298928 | A1 | * | 12/2009 | Iino et al. .................... | 514/452 |

FOREIGN PATENT DOCUMENTS

| | | |
|---|---|---|
| WO | 2008 016356 | 2/2008 |
| WO | 2010 037135 | 4/2010 |

OTHER PUBLICATIONS

Harrison et al. Use of an in Vitro Model of Tissue-Engineered Skin to Investigate the Mechanism of Skin Graft Contraction. Tissue Engineering, 2006. 12(11): 3119-3133.*
"Psoriasis associated human protein SEQ ID No. 20450." Retrieved from EBI accession No. GSP: ARY79583, Database accession No. ARY79583, total pp. 1, XP002657498 (Feb. 7, 2008).
Christelle, C. et al., "Small-Molecule Activators of Insulin-Degrading Enzyme Discovered through High-Throughput Compound Screening", vol. 4, No. 4 XP002657499, ISSN: 1932-6203, (Apr. 4, 2009).
Guo, Q. et al., Molecular basis for the recognition and cleavages of IGF-II, TGF-α, and amylin by human isulin degrading enzyme, J. Mol.Biol., vol. 395, No. 2, pp. 1-23 (Jan. 15, 2010).
Radulescu, R. et al., "Immunohistochemical demonstration of the zinc metalloprotease insulin-degrading enzyme in normal and malignant human breast: Correlation with tissue insulin levels", International Journal of Oncology, vol. 30, pp. 73-80, (2007).
Kim, M. et al., "Decreased Catalytic Activity of the Insulin-degrading Enzyme Chromosome 10-Linked Alzheimer Disease Families", The Journal of Biological Chemistry, vol. 282, No. 11, pp. 7825-7832, (Jan. 22, 2007 ).
Miners, J. S. et al., "Neprilysin and Insulin-Degrading Enzyme Levels Are Increased in Alzheimer Disease in Relation to Disease Severity", J Neuropathol Exp Neurol, vol. 68, No. 8, pp. 902-914, (Aug. 2009).
Groves, C. J. et al., "Association and Haplotype Analysis of the Insulin-Degrading Enzyme (IDE) Gene, a Strong Positional and Biological Candidate for Type 2 Diabetes Susceptibility", Diabetes, vol. 52, pp. 1300-1305,(May 2003).
Shearer, J. D. et al., "Insulin is degraded extracellularly in wounds by insulin-degrading enxyme (EC 3.4.24.56)", Am J. Physiol Endocrinol Metab, vol. 273, pp. E657-E664 (1997).
Ali, M. A. et al., "The Insulin Degrading Enzyme Binding Domain of Varicell-Zoster Virus (VZV) Glycoprotin E is Important for Cell-to-Cell Spread and VZV Infectivity, while a Glycoprotein I Binding Domain is Essential for Infection", Virology, vol. 386, No. 2, pp. 270-279, (Apr. 10, 2009).
International Search Report dated Aug. 22, 2012 in PCT/IB11/05560 Filed Dec. 12, 2011.

(Continued)

*Primary Examiner* — Christopher M Babic
*Assistant Examiner* — Kimberly A. Aron
(74) *Attorney, Agent, or Firm* — Oblon, McClelland, Maier & Neustadt, L.L.P.

(57) ABSTRACT

The subject matter of the present invention is in particular the use of an amino acid sequence of IDE, or of an analogue or fragment thereof, or of at least one nucleic acid sequence encoding this sequence, as a biomarker, or as an active agent, with regard to a dandruff condition of the scalp.

2 Claims, 4 Drawing Sheets

Figure 1:
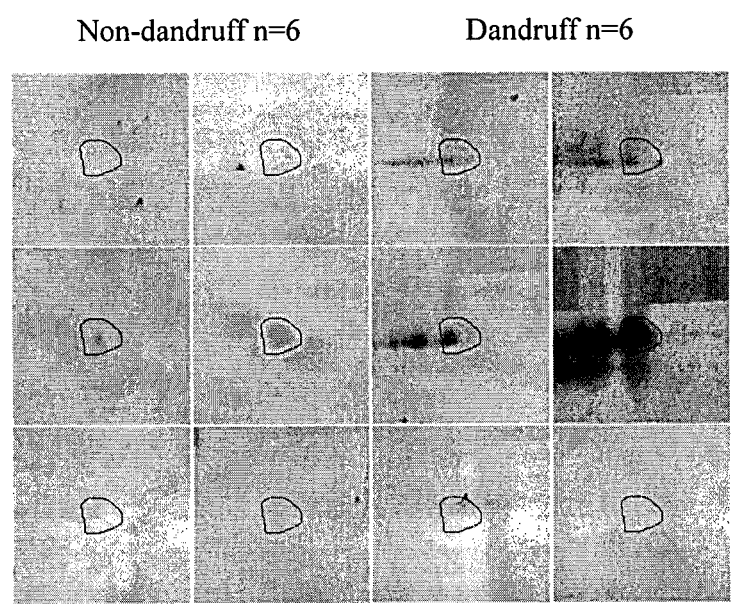

Specification includes a Sequence Listing.

(56) References Cited

OTHER PUBLICATIONS

Written Opinion dated Aug. 22, 2012 in PCT/IB11/05560 Filed Dec. 12, 2011(with computer generated translation).
French Search Report dated Aug. 24, 2011 in French Patent Application No. 1060429 Filed Dec. 13, 2010.
Wakamatsu, A. et al. "NEDO functional analysis of protein and research application project" GenBank: BAG35668.1.

* cited by examiner

SEQUENCE LISTING

```
<160> NUMBER OF SEQ ID NOS: 14

<210> SEQ ID NO 1
<211> LENGTH: 3060
<212> TYPE: DNA
<213> ORGANISM: Homo Sapiens

<400> SEQUENCE: 1
atgcggtacc ggctagcgtg gcttctgcac cccgcactgc ccagcacctt ccgctcagtc     60
ctcggcgccc gcctgccgcc tccggagcgc ctgtgtggtt tccaaaaaaa gacttacagc    120
aaaatgaata atccagccat caagagaata ggaaatcaca ttaccaagtc tcctgaagac    180
aagcgagaat atcgagggct agagctggcc aatggtatca aagtacttct tatcagtgat    240
cccaccacgg ataagtcatc agcagcactt gatgtgcaca taggttcatt gtcggatcct    300
ccaaatattg ctggcttaag tcatttttgt gaacatatgc ttttttggg aacaaagaaa     360 tacccctaaag aaaatgaata cagccagttt ctcagtgagc atgcaggaag ttcaaatgcc   420
tttactagtg gagagcatac caattactat tttgatgttt ctcatgaaca cctagaaggt    480
gccctagaca ggtttgcaca gttttttctg tgcccccttgt tcgatgaaag ttgcaaagac    540
agagaggtga atgcagttga ttcagaacat gagaagaatg tgatgaatga tgcctggaga    600
ctctttcaat tggaaaaagc tacagggaat cctaaacacc ccttcagtaa atttgggaca    660
ggtaacaaat atactctgga gactagacca aaccaagaag gcattgatgt aagacaagag    720
ctactgaaat tccattctgc ttactattca tccaacttaa tggctgtttg tgttttaggt    780
cgagaatctt tagatgactt gactaatctg gtggtaaagt tattttctga agtagagaac    840
aaaaatgttc cattgccaga atttcctgaa caccctttcc aagaagaaca tcttaaacaa    900
ctttacaaaa tagtacccat taaagatatt aggaatctct atgtgacatt tcccatacct    960
gaccttcaga aatactacaa atcaaatcct ggtcattatc ttggtcatct cattgggcat   1020
gaaggtcctg gaagtctgtt atcagaactt aagtcaaagg ctgggttaa tactcttgtt   1080 ggtgggcaga aggaaggagc ccgaggtttt atgttttta tcattaatgt ggacttgacc    1140
gaggaaggat tattacatgt tgaagatata attttgcaca tgtttcaata cattcagaag   1200
ttacgtgcag aaggacctca agaatgggtt ttccaagagt gcaaggactt gaatgctgtt   1260
gcttttaggt ttaaagacaa agagaggcca cggggctata catctaagat tgcaggaata   1320
ttgcattatt atccccctaga agaggtgctc acagcggaat atttactgga agaatttaga   1380
cctgacttaa tagagatggt tctcgataaa ctcagaccag aaaatgtccg ggttgccata   1440
gtttctaaat cttttgaagg aaaaactgat cgcacagaag agtggtatgg aacccagtac    1500
aaacaagaag ctataccgga tgaagtcatc aagaaatggc aaaatgctga cctgaatggg    1560
aaatttaaac ttcctacaaa gaatgaattt attcctacga attttgagat tttaccgtta   1620
gaaaaagagg cgacaccata ccctgctctt attaaggata cagctatgag caaactttgg    1680
ttcaaacaag atgataagtt tttttgccg aaggcttgtc tcaactttga attttcagc    1740
```

-continued

```
ccatttgctt atgtggaccc cttgcactgt aacatggcct atttgtacct tgagctcctc     1800
aaagactcac tcaacgagta tgcatatgca gcagagctag caggcttgag ctatgatctc     1860
caaaatacca tctatgggat gtatctttca gtgaaaggtt acaatgacaa gcagccaatt     1920
ttactaaaga agattattga gaaaatggct acctttgaga ttgatgaaaa agatttgaa      1980 attatcaaag aagcatatat gcgatctctt aacaatttcc gggctgaaca gcctcaccag     2040
catgccatgt actacctccg cttgctgatg actgaagtgg cctggactaa agatgagtta     2100
aaagaagctc tggatgatgt aacccttcct cgccttaagg ccttcatacc tcagctcctg     2160
tcacggctgc acattgaagc ccttctccat ggaaacataa caaagcaggc tgcattagga     2220
attatgcaga tggttgaaga caccctcatt gaacatgctc ataccaaacc tctccttcca     2280
agtcagctgg ttcggtatag agaagttcag ctccctgaca gaggatggtt tgtttatcag     2340
cagagaaatg aagttcacaa taactgtggc atcgagatat actaccaaac agacatgcaa     2400
agcacctcag agaatatgtt tctggagctc ttctgtcaga ttatctcgga accttgcttc     2460
aacaccctgc gcaccaagga gcagttgggc tatatcgtct tcagcgggcc acgtcgagct     2520
aatggcatac agggcttgag attcatcatc cagtcagaaa agccacctca ctacctagaa     2580
agcagagtgg aagctttctt aattaccatg gaaaagtcca tagaggacat gacagaagag     2640
gccttccaaa aacacattca ggcattagca attcgtcgac tagacaaacc aaagaagcta     2700
tctgctgagt gtgctaaata ctggggagaa atcatctccc agcaatataa ttttgacaga     2760
gataacactg aggttgcata tttaaagaca cttaccaagg aagatatcat caaattctac     2820
aaggaaatgt tggcagtaga tgctccaagg agacataagg tatccgtcca tgttcttgcc     2880
agggaaatgg attcttgtcc tgttgttgga gagttcccat gtcaaaatga cataaatttg     2940
tcacaagcac cagccttgcc acaacctgaa gtgattcaga acatgaccga attcaagcgt     3000
ggtctgccac tgtttccccct tgtgaaacca catattaact tcatggctgc aaaactctga    3060
```

<210> SEQ ID NO 2
<211> LENGTH: 60
<212> TYPE: DNA
<213> ORGANISM: Homo Sapiens

<400> SEQUENCE: 2

```
gggctagagc tggccaatgg tatcaaagta cttcttatca gtgatcccac cacggataag     60
```

<210> SEQ ID NO 3
<211> LENGTH: 60
<212> TYPE: DNA
<213> ORGANISM: Homo Sapiens

<400> SEQUENCE: 3

```
gaatctttag atgacttgac taatctggtg gtaaagttat tttctgaagt agagaacaaa     60
```

<210> SEQ ID NO 4
<211> LENGTH: 36
<212> TYPE: DNA
<213> ORGANISM: Homo Sapiens

<400> SEQUENCE: 4

```
ggttacaatg acaagcagcc aattttacta aagaag                              36
```

<210> SEQ ID NO 5
<211> LENGTH: 27
<212> TYPE: DNA
<213> ORGANISM: Homo Sapiens

<400> SEQUENCE: 5
atggctacct ttgagattga tgaaaaa                                27

<210> SEQ ID NO 6
<211> LENGTH: 204
<212> TYPE: DNA
<213> ORGANISM: Homo Sapiens

<400> SEQUENCE: 6
accaaggagc agttgggcta tatcgtcttc agcgggccac gtcgagctaa tggcatacag      60
ggcttgagat tcatcatcca gtcagaaaag ccacctcact acctagaaag cagagtggaa     120
gctttcttaa ttaccatgga aaagtccata gaggacatga cagaagaggc cttccaaaaa     180
cacattcagg cattagcaat tcgt                                            204

<210> SEQ ID NO 7
<211> LENGTH: 63
<212> TYPE: DNA
<213> ORGANISM: Homo Sapiens

<400> SEQUENCE: 7
acacttacca aggaagatat catcaaattc tacaaggaaa tgttggcagt agatgctcca      60
agg                                                                    63

<210> SEQ ID NO 8
<211> LENGTH: 1019
<212> TYPE: PRT
<213> ORGANISM: Homo Sapiens

<400> SEQUENCE: 8

Met Arg Tyr Arg Leu Ala Trp Leu Leu His Pro Ala Leu Pro Ser Thr
1               5                   10                  15

Phe Arg Ser Val Leu Gly Ala Arg Leu Pro Pro Glu Arg Leu Cys
            20                  25                  30

Gly Phe Gln Lys Lys Thr Tyr Ser Lys Met Asn Asn Pro Ala Ile Lys
        35                  40                  45

Arg Ile Gly Asn His Ile Thr Lys Ser Pro Glu Asp Lys Arg Glu Tyr
    50                  55                  60

Arg Gly Leu Glu Leu Ala Asn Gly Ile Lys Val Leu Leu Ile Ser Asp
65                  70                  75                  80

Pro Thr Thr Asp Lys Ser Ser Ala Ala Leu Asp Val His Ile Gly Ser
                85                  90                  95

Leu Ser Asp Pro Pro Asn Ile Ala Gly Leu Ser His Phe Cys Glu His
            100                 105                 110

Met Leu Phe Leu Gly Thr Lys Lys Tyr Pro Lys Glu Asn Glu Tyr Ser
        115                 120                 125

Gln Phe Leu Ser Glu His Ala Gly Ser Ser Asn Ala Phe Thr Ser Gly
    130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Glu
                165                 170                 175

Ser Cys Lys Asp Arg Glu Val Asn Ala Val Asp Ser Glu His Glu Lys
            180                 185                 190

Asn Val Met Asn Asp Ala Trp Arg Leu Phe Gln Leu Glu Lys Ala Thr
        195                 200                 205

-continued

Gly Asn Pro Lys His Pro Phe Ser Lys Phe Gly Thr Gly Asn Lys Tyr
    210             215                 220

Thr Leu Glu Thr Arg Pro Asn Gln Glu Gly Ile Asp Val Arg Gln Glu
225                 230                 235                 240

Leu Leu Lys Phe His Ser Ala Tyr Tyr Ser Ser Asn Leu Met Ala Val
                245                 250                 255

Cys Val Leu Gly Arg Glu Ser Leu Asp Asp Leu Thr Asn Leu Val Val
                260                 265                 270

Lys Leu Phe Ser Glu Val Glu Asn Lys Asn Val Pro Leu Pro Glu Phe
            275                 280                 285

Pro Glu His Pro Phe Gln Glu His Leu Lys Gln Leu Tyr Lys Ile
            290                 295                 300

Val Pro Ile Lys Asp Ile Arg Asn Leu Tyr Val Thr Phe Pro Ile Pro
305                 310                 315                 320

Asp Leu Gln Lys Tyr Tyr Lys Ser Asn Pro Gly His Tyr Leu Gly His
                325                 330                 335

Leu Ile Gly His Glu Gly Pro Gly Ser Leu Leu Ser Glu Leu Lys Ser
                340                 345                 350

Lys Gly Trp Val Asn Thr Leu Val Gly Gly Lys Glu Gly Ala Arg
            355                 360                 365

Gly Phe Met Phe Phe Ile Ile Asn Val Asp Leu Thr Glu Glu Gly Leu
    370                 375                 380

Leu His Val Glu Asp Ile Ile Leu His Met Phe Gln Tyr Ile Gln Lys
385                 390                 395                 400

Leu Arg Ala Glu Gly Pro Gln Glu Trp Val Phe Gln Glu Cys Lys Asp
                405                 410                 415

Leu Asn Ala Val Ala Phe Arg Phe Lys Asp Lys Glu Arg Pro Arg Gly
            420                 425                 430

Tyr Thr Ser Lys Ile Ala Gly Ile Leu His Tyr Tyr Pro Leu Glu Glu
            435                 440                 445

Val Leu Thr Ala Glu Tyr Leu Leu Glu Glu Phe Arg Pro Asp Leu Ile
450                 455                 460

Glu Met Val Leu Asp Lys Leu Arg Pro Glu Asn Val Arg Val Ala Ile
465                 470                 475                 480

Val Ser Lys Ser Phe Glu Gly Lys Thr Asp Arg Thr Glu Glu Trp Tyr
                485                 490                 495

Gly Thr Gln Tyr Lys Gln Glu Ala Ile Pro Asp Glu Val Ile Lys Lys
            500                 505                 510

Trp Gln Asn Ala Asp Leu Asn Gly Lys Phe Lys Leu Pro Thr Lys Asn
            515                 520                 525

Glu Phe Ile Pro Thr Asn Phe Glu Ile Leu Pro Leu Glu Lys Glu Ala
    530                 535                 540

Thr Pro Tyr Pro Ala Leu Ile Lys Asp Thr Ala Met Ser Lys Leu Trp
545                 550                 555                 560

Phe Lys Gln Asp Asp Lys Phe Leu Pro Lys Ala Cys Leu Asn Phe
                565                 570                 575

Glu Phe Phe Ser Pro Phe Ala Tyr Val Asp Pro Leu His Cys Asn Met
                580                 585                 590

Ala Tyr Leu Tyr Leu Glu Leu Leu Lys Asp Ser Leu Asn Glu Tyr Ala
            595                 600                 605

Tyr Ala Ala Glu Leu Ala Gly Leu Ser Tyr Asp Leu Gln Asn Thr Ile
610                 615                 620

```
Tyr Gly Met Tyr Leu Ser Val Lys Gly Tyr Asn Asp Lys Gln Pro Ile
625                 630                 635                 640

Leu Leu Lys Lys Ile Ile Glu Lys Met Ala Thr Phe Glu Ile Asp Glu
            645                 650                 655

Lys Arg Phe Glu Ile Ile Lys Glu Ala Tyr Met Arg Ser Leu Asn Asn
        660                 665                 670

Phe Arg Ala Glu Gln Pro His Gln His Ala Met Tyr Tyr Leu Arg Leu
    675                 680                 685

Leu Met Thr Glu Val Ala Trp Thr Lys Asp Glu Leu Lys Glu Ala Leu
690                 695                 700

Asp Asp Val Thr Leu Pro Arg Leu Lys Ala Phe Ile Pro Gln Leu Leu
705                 710                 715                 720

Ser Arg Leu His Ile Glu Ala Leu Leu His Gly Asn Ile Thr Lys Gln
                725                 730                 735

Ala Ala Leu Gly Ile Met Gln Met Val Glu Asp Thr Leu Ile Glu His
            740                 745                 750

Ala His Thr Lys Pro Leu Leu Pro Ser Gln Leu Val Arg Tyr Arg Glu
        755                 760                 765

Val Gln Leu Pro Asp Arg Gly Trp Phe Val Tyr Gln Gln Arg Asn Glu
770                 775                 780

Val His Asn Asn Cys Gly Ile Glu Ile Tyr Tyr Gln Thr Asp Met Gln
785                 790                 795                 800

Ser Thr Ser Glu Asn Met Phe Leu Glu Leu Phe Cys Gln Ile Ile Ser
                805                 810                 815

Glu Pro Cys Phe Asn Thr Leu Arg Thr Lys Glu Gln Leu Gly Tyr Ile
            820                 825                 830

Val Phe Ser Gly Pro Arg Arg Ala Asn Gly Ile Gln Gly Leu Arg Phe
        835                 840                 845

Ile Ile Gln Ser Glu Lys Pro Pro His Tyr Leu Glu Ser Arg Val Glu
850                 855                 860

Ala Phe Leu Ile Thr Met Glu Lys Ser Ile Glu Asp Met Thr Glu Glu
865                 870                 875                 880

Ala Phe Gln Lys His Ile Gln Ala Leu Ala Ile Arg Arg Leu Asp Lys
                885                 890                 895

Pro Lys Lys Leu Ser Ala Glu Cys Ala Lys Tyr Trp Gly Glu Ile Ile
            900                 905                 910

Ser Gln Gln Tyr Asn Phe Asp Arg Asp Asn Thr Glu Val Ala Tyr Leu
        915                 920                 925

Lys Thr Leu Thr Lys Glu Asp Ile Ile Lys Phe Tyr Lys Glu Met Leu
930                 935                 940

Ala Val Asp Ala Pro Arg Arg His Lys Val Ser Val His Val Leu Ala
945                 950                 955                 960

Arg Glu Met Asp Ser Cys Pro Val Val Gly Glu Phe Pro Cys Gln Asn
                965                 970                 975

Asp Ile Asn Leu Ser Gln Ala Pro Ala Leu Pro Gln Pro Glu Val Ile
            980                 985                 990

Gln Asn Met Thr Glu Phe Lys Arg Gly Leu Pro Leu Phe Pro Leu Val
        995                 1000                1005

Lys Pro His Ile Asn Phe Met Ala Ala Lys Leu
    1010                1015

<210> SEQ ID NO 9
<211> LENGTH: 20
<212> TYPE: PRT
```

<213> ORGANISM: Homo Sapiens

<400> SEQUENCE: 9

Gly Leu Glu Leu Ala Asn Gly Ile Lys Val Leu Leu Ile Ser Asp Pro
1               5                   10                  15

Thr Thr Asp Lys
            20

<210> SEQ ID NO 10
<211> LENGTH: 20
<212> TYPE: PRT
<213> ORGANISM: Homo Sapiens

<400> SEQUENCE: 10

Glu Ser Leu Asp Asp Leu Thr Asn Leu Val Val Lys Leu Phe Ser Glu
1               5                   10                  15

Val Glu Asn Lys
            20

<210> SEQ ID NO 11
<211> LENGTH: 12
<212> TYPE: PRT
<213> ORGANISM: Homo Sapiens

<400> SEQUENCE: 11

Gly Tyr Asn Asp Lys Gln Pro Ile Leu Leu Lys Lys
1               5                   10

<210> SEQ ID NO 12
<211> LENGTH: 9
<212> TYPE: PRT
<213> ORGANISM: Homo Sapiens

<400> SEQUENCE: 12

Met Ala Thr Phe Glu Ile Asp Glu Lys
1               5

<210> SEQ ID NO 13
<211> LENGTH: 68
<212> TYPE: PRT
<213> ORGANISM: Homo Sapiens

<400> SEQUENCE: 13

Thr Lys Glu Gln Leu Gly Tyr Ile Val Phe Ser Gly Pro Arg Arg Ala
1               5                   10                  15

Asn Gly Ile Gln Gly Leu Arg Phe Ile Ile Gln Ser Glu Lys Pro Pro
            20                  25                  30

His Tyr Leu Glu Ser Arg Val Glu Ala Phe Leu Ile Thr Met Glu Lys
        35                  40                  45

Ser Ile Glu Asp Met Thr Glu Glu Ala Phe Gln Lys His Ile Gln Ala
    50                  55                  60

Leu Ala Ile Arg
65

<210> SEQ ID NO 14
<211> LENGTH: 21
<212> TYPE: PRT
<213> ORGANISM: Homo Sapiens

```
<400> SEQUENCE: 14

Thr Leu Thr Lys Glu Asp Ile Ile Lys Phe Tyr Lys Glu Met Leu Ala
1               5                   10                  15

Val Asp Ala Pro Arg
            20
```

USE OF IDE AS A BIOMARKER FOR A SCALP CONDITION

The present invention relates to the field of cosmetic and/or therapeutic biomarkers and targets for the skin, in particular for a dandruff condition of the scalp, and also to the use thereof as active agents.

For the purposes of the invention, the term "skin" means the entire epidermis of a human body, including mucous membranes and areas of skin covered with bodily hair or head hair. More particularly, the skin considered in the present invention is preferably the lips and the skin of the face, the neckline or the scalp, and even more preferably the skin of the scalp.

The skin is a tissue in which the cells are joined together and integrally attached to each other. It forms an outer coating comprising sebaceous or sweat glands, and hair follicles. The skin and, in particular, the scalp are epithelia which undergo continual renewal. The renewal, or desquamation, is a coordinated and finely regulated process resulting in the imperceptible and invisible removal of the superficial cells.

However, abnormal or irregular desquamation of the cells of the stratum corneum, for various reasons, can result in the formation of large, thick cell clusters which are visible to the naked eye and called "squamae" or "dandruff" in the case of the scalp, or in other situations in a thinning of the stratum corneum. Desquamation disorders, resulting from abnormal or irregular desquamation, can result in fragility or even in a lack of the barrier properties of the epidermis.

By way of example of factors which promote the appearance of squamae or dandruff, mention may be made of stress, the winter period, an excess of sebum, a hydration defect or colonization of the skin or the hair follicles by the yeast *Malassezia* sp. These factors especially have the common feature of causing and/or promoting skin inflammation. Such an inflammation reinforces the appearance or even increases the presence of squamae or of dandruff. In particular, yeasts of *Malassezia* sp. type, which make up part of the normal commensal flora at the surface of the scalp in dandruff-free individuals, experience a substantial increase in their proportion in the case of dandruff, or in the case of associated seborrheic dermatitis. Imbalance of the scalp ecoflora is a factor that promotes or even reinforces the presence of dandruff.

The presence of squamae or dandruff conditions can be recurring, frequent, chronic conditions which are socially debilitating owing to their obvious unsightly nature. What is more, dandruff conditions of the scalp or abnormal desquamation of the skin can be reflected by an impairment of the barrier function of the epidermis, or generate itching sensations or pruritus, resulting in scratching which amplifies the phenomenon of the appearance of squamae or dandruff, and, in return, irritation of the scalp or the skin.

The dandruff conditions of the scalp may be of greasy type or of dry type. Dry dandruff conditions of the scalp are more frequently manifested, and are amplified, during skin hydration disorders, and especially during substantial dryness of the scalp epidermis. In addition, since the scalp is rich in sebaceous glands, a dandruff condition can develop more readily in the excessive presence of sebum and be more readily pruriginous. Thus, an excessive secretion of sebum, or hyperseborrhea, promotes the appearance of a greasy dandruff condition of the scalp, or greasy dandruff, generally associated with displeasure, sensations of discomfort, esthetic disorders, or even a cutaneous pathology.

Dandruff conditions generally respond to various local or systemic treatments. However, the efficacy of these treatments is only suspensory and demands rigorous adherence on the part of the user (sufficient frequency of use and sufficient application time). However, daily and long-term use of these treatments can lead to a phenomenon of habituation, reducing their efficacy, and generally being associated with a rebound phenomenon occurring when the treatment is stopped. This phenomenon manifests itself through hyperseborrhea, which worsens the dandruff condition and impairs the barrier function of the scalp. Moreover, the aggressiveness of certain antidandruff active agents with respect to the epidermal cells or the scalp ecoflora may also affect the scalp's barrier functions and lead to worsening of the dandruff condition. Finally, the efficacy of antidandruff treatments is often slow to develop and requires rigorous application over the long term. This lag time often leads to failure to follow the treatment. Consequently, many failures arise in the use of these treatments.

Many epidermal factors, the expression, biological activity or maturation of which are modified, decreased or increased, are known to be involved, directly or indirectly, in the process of renewal or desquamation of the skin, and especially of the scalp.

These factors can be used as biomarkers for the skin, as screening targets, or even as cosmetic active agents.

However, many unknown factors still remain regarding the intimate mechanism and the factors involved in desquamation of the skin, and in particular in the onset of dandruff.

There is thus a need for novel biomarkers for characterizing desquamation of the skin, and more particularly a dandruff condition of the scalp.

There is also a need for novel targets for screening active agents or physical treatments for caring for the skin, in particular for preventing and/or treating a skin desquamation disorder, and more particularly a dandruff condition of the scalp.

There is also a need for novel active agents or novel treatments for preventing and/or treating a skin desquamation disorder, and more particularly a dandruff condition of the scalp.

There is also a need for novel cosmetic targets for caring for the skin, in particular for preventing and/or treating a skin desquamation disorder, and more particularly a dandruff condition of the scalp.

There is also still a need for novel cosmetic treatments for preventing, reducing and/or treating dandruff conditions of the scalp, which are efficient and free of side effects liable to adversely affect good adherence to the treatment.

There is also a need for a treatment for dandruff conditions of the scalp that does not adversely affect the ecoflora of the scalp, or even that reinforces the presence of a healthy ecoflora.

There is also a need for a treatment for dandruff conditions that is capable of maintaining, or even reinforcing, the hydration of the scalp.

There is a need for a treatment for dandruff conditions that is capable of maintaining, or even reinforcing, the barrier properties of the scalp.

There is a need for treatments for dandruff conditions that are free of the abovementioned side effects, and in particular that do not induce hyperseborrhea, seborrheic dermatitis or pruriginous conditions.

There is also a need for a treatment for dandruff conditions that does not induce inflammation.

It is an object of the present invention to satisfy these needs.

Thus, according to one of its first subjects, the present invention relates to the use (i) of at least one amino acid sequence encoded by a nucleic acid sequence represented by SEQ ID No.: 1, or an analog or fragment of SEQ ID No.: 1, or (ii) of at least said nucleic acid sequence, for screening active agents or physical treatments that are capable of modulating the activity, expression or maturation of said amino acid sequence or of said nucleic acid sequence, for preventing and/or treating abnormal desquamation of the skin, and preferably a dandruff condition of the scalp.

Unexpectedly, in the course of a 2D difference electrophoresis proteomic analysis, the inventors have observed, using noninvasive scalp samples, that insulin-degrading enzyme, or insulysine, or insulinase or IDE, proves to be a sensitive and specific biomarker of a dandruff condition of the scalp.

More specifically, the inventors have observed that the level of expression of IDE, and more particularly of peptides derived from IDE and identified by the sequences SEQ ID No.: 8 to SEQ ID No.: 14, was systematically increased in the scalps presenting a dandruff condition when compared with the dandruff-free scalps. This is the first time that a relationship has been established between a variation in IDE expression and abnormal desquamation of a skin. Thus, to the inventors' knowledge, this enzyme has never been identified as a marker of abnormal desquamation, and even less so of a dandruff condition.

This observation validates the use of IDE or of peptide fragments derived therefrom, or of nucleic acids encoding these polypeptides, as skin biomarker or for the screening of novel agents that are active toward abnormal desquamation of the skin, and especially dandruff conditions, and also the use of agents for modulating the activity of this enzyme, for the prevention and/or treatment of a dandruff condition of the scalp.

For the purposes of the invention, the term "expression" means, with regard to an amino acid sequence, for example a protein or a peptide, or to a nucleic acid sequence, for example an mRNA, its content or the variation of its content relative to a reference.

For the purposes of the invention, the term "maturation" means, with regard to an amino acid sequence, for example a protein or a peptide, or to a nucleic acid sequence, for example an mRNA, the modifications which follow their synthesis in a cell environment. For example, in the case of an amino acid sequence, the term "maturation" means the post-translational modifications, such as glycosylation, farnesylation or acetylation of certain amino acids, or the proteolytic steps resulting in the elimination of "signal" or "secretory" sequences or in the release of sequences having particular biological properties. In the case of a nucleic acid sequence, the term "maturation" means, for example, the alternative splicing of a pre-mRNA.

For the purposes of the invention, the term "activity" means, with regard to an amino acid sequence, for example a protein or a peptide, the biological activity of the amino acid sequence, where appropriate after maturation, such as an enzymatic activity, an agonist or antagonist activity with respect to a receptor, an enzyme-activating or -inhibiting activity, or a "structural" activity.

More particularly, for the purposes of the invention, the term "activity" with regard to an amino acid sequence of the invention represented by SEQ ID No. 8 means its proteolytic activity, especially with regard to its usual substrates, such as insulin, glucagon, bradykinin or kallidin.

For the purposes of the invention, the term "activity" means, with regard to a nucleic acid sequence, for example an mRNA, its translation.

IDE, also known as insulysine or insulinase, is a zinc metalloprotease (P14735; EC=3.4.24.56) of 1019 amino acids and of 110 kDa, which belongs to the M16A protease family. It is involved in the hydrolysis of small bioactive peptides, such as insulin, β-amyloid, amylin, glucagon, insulin growth factor II (IGF-II), β-endorphin, somatostatin and atrial natriuretic peptide (Guo et al. 2009).

The expression of IDE is particularly abundant in the brain, the liver and muscles, and has especially been localized in the granular layer and is described as being present in the stratum corneum (Radulescu et al., 2007). IDE has particularly been implicated in the degradation of the β-amyloid deposits characteristic of Alzheimer's disease (Kim et al. 2007; Miners et al. 2009). It is also involved in the pathology of type II diabetes and hyperinsulinemia (Groves et al. 2003).

It is also described as being associated with cicatrization defects in epithelia, which may be compensated for by supplying insulin and by IDE inhibitors (Shearer et al. 1997). IDE may also be associated with a viral sensitivity (Ali et al. 2009).

According to yet another of its subjects, the present invention relates to the cosmetic use of an effective amount of at least one agent that modulates the activity, expression or maturation of an amino acid sequence of the invention, or of a nucleic acid sequence of the invention, as an active agent for preventing and/or treating a disorder of the barrier properties of the scalp.

Preferably, a modulatory agent is an agent that inhibits the enzymatic activity of an amino acid sequence of the invention.

More preferably, such an inhibitory agent may be used for preventing and/or treating a dandruff condition of the scalp.

For the purposes of the present invention, the term "effective amount" of a compound of the invention means an amount of this compound that is sufficient and necessary for obtaining a desired effect, and more particularly a cosmetic or care effect with regard to abnormal or irregular desquamation of the skin, and preferably a dandruff condition of the scalp.

For the purposes of the invention, the term "preventing" means reducing the risk of occurrence or slowing down the occurrence of a given phenomenon, namely, in the present invention, abnormal or irregular desquamation of the skin, and preferably a dandruff condition of the scalp.

According to yet another of its subjects, the present invention relates to the use (i) of at least one amino acid sequence of the invention, or (ii) of at least one nucleic acid sequence of the invention, as a biomarker for desquamation of the skin, and preferably a dandruff condition of the scalp.

For the purposes of the invention, the term "biomarker" means a molecule or the activity of a molecule, the presence or absence, the content or the degree of activity of which, or a variation of these parameters, is characteristic of a biological, physiological or pathological process, or of the impact or the effect induced by the administration of an active agent or of a physical treatment on such a process.

According to another of its subjects, the present invention relates to the use (i) of at least one amino acid sequence of the invention, or (ii) of at least one nucleic acid sequence of the invention, for characterizing the efficacy of a cosmetic treatment for the skin.

According to a preferred embodiment, a cosmetic treatment whose efficacy is characterized may be a cosmetic treatment of abnormal desquamation of the skin, and preferably a dandruff condition of the scalp.

According to another embodiment, the present invention relates to the use (i) of at least one amino acid sequence of the invention, or (ii) of at least one nucleic acid sequence of the invention, for selecting, from among a set of active agents known for preventing and/or treating abnormal desquamation of the skin, and preferably a dandruff condition of the scalp, an active agent presumed to exert a maximum beneficial effect with regard to said desquamation or said dandruff condition.

According to yet another of its subjects, the present invention relates to the use of an effective amount (i) of at least one amino acid sequence of the invention, or (ii) of at least one nucleic acid sequence of the invention, or (iii) of at least one modulatory agent of the invention, for preparing an isolated reconstructed skin.

Advantageously, a model of isolated skin of the invention may be used to reproduce a skin desquamation disorder, and especially a dandruff condition of the scalp.

According to yet another of its subjects, the present invention relates to a process for characterizing abnormal desquamation of the skin, and preferably a dandruff condition of the scalp, comprising at least the steps consisting in:
  a) performing, in an isolated sample of a skin, and preferably of a scalp, a qualitative or quantitative measurement of the expression, maturation or activity of said amino acid sequence or of said nucleic acid sequence, and
  b) comparing said measurement carried out in step a) with a reference measurement.

According to yet another of its subjects, the present invention relates to a process for the screening of active agents or of physical treatments that are capable of modulating the activity, expression or maturation of an amino acid sequence of the invention, or of a nucleic acid sequence of the invention, for preventing and/or treating abnormal desquamation of the skin, and preferably a dandruff condition of the scalp, comprising at least the steps consisting in:
  a) placing said amino acid sequence or said nucleic acid sequence under conditions favorable for the activity, expression or maturation of said sequences,
  b) bringing said amino acid sequence or said nucleic acid sequence into contact with at least one active agent to be tested, or exposing said amino acid sequence or said nucleic acid sequence to a physical treatment to be tested,
  c) performing a qualitative or quantitative measurement of the expression, maturation or activity of said amino acid sequence or of said nucleic acid sequence, and
  d) comparing said measurement with a reference measurement.

According to yet another of these subjects, the present invention relates to a cosmetic process for preventing and/or treating abnormal desquamation of the skin, and preferably a dandruff condition of the scalp, in an individual in need thereof, comprising at least one step that consists in administering to said individual at least one composition comprising, as active agent, at least one agent that modulates the activity, expression or maturation of said sequences, preferably as defined below.

According to yet another of these subjects, the present invention relates to a cosmetic process for characterizing the efficacy of a cosmetic treatment of abnormal desquamation of the skin, and preferably a dandruff condition of the scalp, in an individual in need thereof, comprising at least the steps consisting in:

a) performing, before implementing the cosmetic treatment, in a first isolated skin sample, preferably an isolated scalp sample, taken from said individual, at least a first qualitative or quantitative measurement of the expression, maturation or activity of at least one amino acid sequence of the invention or of at least one nucleic acid sequence of the invention,
  b) performing, after implementing the cosmetic treatment, in a second isolated skin sample, preferably an isolated scalp sample, taken from said individual, at least a second qualitative or quantitative measurement of the expression, maturation or activity of said amino acid sequence or of said nucleic acid sequence, and
  c) comparing the first and second measurements, in particular in order to deduce therefrom information relating to at least one effect of the implementation of the cosmetic treatment.

According to one preferred embodiment, a process or use in accordance with the invention can be carried out in vivo, in vitro, or ex vivo, and even more preferably in vitro or ex vivo.

According to yet another embodiment, the present invention relates to an isolated peptide represented by an amino acid sequence chosen from SEQ ID No.: 9 to SEQ ID No.: 14, or an analog or fragment thereof.

According to yet another of these subjects, the present invention relates to a composition comprising a peptide represented by an amino acid sequence chosen from SEQ ID No.: 8 to SEQ ID No.: 14, or an analog or fragment thereof, or a nucleic acid sequence encoding such a peptide.

According to yet another of these subjects of the present invention relates to a multicellular skin model comprising at least one cell in which the expression of a protein represented by SEQ ID No.: 8, or a fragment or analog thereof, is repressed or increased. Preferably, such a cellular model is an in vitro or ex vivo model.

The present invention has the advantage of proposing a novel sensitive and specific biomarker for the skin, and in particular for desquamation, especially abnormal desquamation, of the skin, and more particularly for a dandruff condition of the scalp.

The observation of the presence of IDE in the stratum corneum, and more particularly of peptides derived specifically from this protein, makes advantageously possible a quantitative or qualitative determination of the expression or of the activity of this protein, or of the corresponding peptides, by simply taking a topical sample.

The sampling method may, for example, be a technique of corneodisc or stripping type, consisting in applying an adhesive element to the epidermis under consideration. When this adhesive element is detached, a fraction of the skin surface is removed. After protein extraction, the latter can then be analyzed by conventional methods, such as ELISA immunoenzymatic assay or Western blot analysis, or more particularly by 2D difference electrophoresis proteomic analysis.

Similarly, the present invention has the advantage of being able to provide a novel biomarker that is suitable for the screening of novel active agents or novel physical treatments for preventing and/or treating a skin desquamation disorder, and especially a dandruff condition of the scalp.

Similarly, according to another advantage, the present invention provides novel active agents for preventing and/or treating a skin desquamation disorder, and especially a dandruff condition of the scalp.

Advantageously, the novel active agents proposed by the present invention reinforce the barrier properties of the scalp.

The protection and reinforcement of the barrier properties of the scalp allow a reduction of the skin inflammation, the maintenance of a balanced barrier, integrity of the barrier and conservation of a balanced ecoflora.

The scalp is then less irritated and pruriginous, less fragile and more hydrated, and the level of dandruff is reduced.

Amino Acid and Nucleic Acid Sequences

Insulin-degrading enzyme (IDE) or insulysine is a protein of 1019 amino acids (SEQ ID No.: 8) comprising an initiating methionine which is removed, and the gene of which is located on chromosome 10, locus 10q23-q25.

Unless otherwise indicated, the term "IDE" is intended to denote in the present patent application the amino acid sequences represented by SEQ ID No.: 8 to SEQ ID No.: 14, possibly having undergone post-translational maturation.

According to a preferred embodiment, the term "IDE" is more particularly intended to denote the amino acid sequence represented by SEQ ID No.: 8, and more preferably the amino acid sequence represented by a sequence derived from SEQ ID No.: 8 in which the initiating methionine has been removed.

According to one embodiment, an amino acid sequence suitable for the invention can be encoded by a nucleic acid sequence represented by SEQ ID No.: 1, or an analog or fragment of this sequence.

The term "analog" of an amino acid sequence or of a nucleic acid sequence in accordance with the invention is intended to denote any amino acid sequence or nucleic acid sequence having sequence identity of at least 85%, preferably at least 90% and more preferentially at least 95% with said reference sequence, and, depending on the case, having biological activity of the same nature or encoding an amino acid sequence having biological activity of the same nature. As analogs that are suitable for use in the invention, mention may be made of the homologous sequences identified in the database Homologene (http://www.ncbi.nlm.nih.gov/homologene). The term "analog of a nucleic acid sequence" is intended in particular to denote a nucleic acid sequence resulting from the degeneracy of the nucleic acid code, and encoding an amino acid sequence in accordance with the invention, in particular as previously defined.

The term "biological activity of the same nature" with regard to an amino acid sequence according to the invention especially means the proteolytic properties usually attributed to IDE, for instance the capacity to hydrolyze insulin, bradykinin, kallidin, β-amyloid peptide or glucagon. In particular, an amino acid sequence according to the invention is more particularly characterized by its capacity to degrade substrates forming structures of amyloid type.

The sequence identity can be determined by visual comparison or by means of any computer tool generally used in the field, such as the BLAST programs available on www.ncbi.nlm.nih.gov and used with the default parameters.

An analog of an amino acid sequence in accordance with the invention may be a peptidomimetic agent.

An analog of an amino acid sequence of the invention can result from modifications resulting from one or more mutation(s) and/or variation(s) in the sequences of the peptides according to the invention originating either from the deletion or the insertion of one or more amino acids, or from the substitution of one or more amino acids, or else from alternative splicing. Several of these modifications can be combined.

Advantageously, an analog of an amino acid sequence of the invention can comprise conservative substitutions compared with this reference amino acid sequence.

By way of example of mutations that can be considered in the present invention, mention may be made, nonexhaustively, of the replacement of one or more amino acid residues with amino acid residues having a similar hydropathic index without, however, substantially affecting the biological properties of the polypeptide. The hydropathic index is an index assigned to amino acids according to their hydrophobicity and their charge (Kyte et al. 1982).

An amino acid sequence or an analog thereof targeted by the present invention can be an amino acid sequence having undergone one or more post-translational maturation(s).

The term "post-translational maturation(s)" is intended to encompass all the modifications that an amino acid sequence is liable to undergo at the end of its synthesis in a cell, such as, for example, one or more phosphorylation(s), one or more thiolation(s), one or more acetylation(s), one or more glycosylation(s), one or more lipidation(s), such as a farnesylation or a palmitoylation, a structural rearrangement such as disulfide bridge formation and/or such as cleavage within the peptide sequence.

An analog of an amino acid sequence has, moreover, substantially the same biological activity as this amino acid sequence.

It is, moreover, known that a primary amino acid sequence can comprise sites specifically recognized by protease-type enzymes, such as trypsin, which, once these sites have actually been recognized, will induce the cleavage of the sequence by proteolysis. This proteolysis results in the production of various peptides, or fragments of amino acid sequences of the invention.

Consequently, the invention also extends to the IDE fragments resulting, where appropriate, from its proteolysis.

For the purposes of the invention, the expression "fragment of an amino acid sequence" means any portion of the amino acid sequence in accordance with the invention comprising at least 3, or even at least 4 and better still at least 6 consecutive amino acids of said reference sequence, or comprising from 3 to 100 consecutive amino acids of said reference sequence, preferably from 4 to 90, preferably from 6 to 80 and more preferentially from 9 to 70 consecutive amino acids of said sequence, and having biological activity of the same nature.

For the purposes of the present invention, the term "fragment of a nucleic acid sequence" means a nucleic acid sequence comprising at least 9, or even at least 12 and better still at least 18 consecutive base pairs of said reference sequence, or comprising from 9 to 300 consecutive base pairs of said reference sequence, preferably from 12 to 270, preferably from 18 to 240 and more preferentially from 27 to 210 consecutive base pairs of said sequence, and encoding an amino acid sequence having biological activity of the same nature as the amino acid sequence encoded by said sequence.

According to one embodiment, an amino acid sequence suitable for the invention can be an amino acid sequence represented by a sequence chosen from SEQ ID No.: 8 to 14, or an analog or fragment thereof, and preferably from SEQ ID No.: 9, SEQ ID No.: 10, SEQ ID No.: 11, SEQ ID No.: 12, SEQ ID No.: 13 and SEQ ID No.: 14, or an analog or fragment thereof.

According to another embodiment, an amino acid sequence that is suitable for use in the invention may be a natural or synthetic amino acid sequence, which can be obtained, where appropriate, after enzymatic or chemical lysis of IDE or by chemical or biological synthesis or by extraction from a biological tissue, for instance the skin, naturally expressing this amino acid sequence or after transfection thereof, and also the various post-translational forms thereof, or else any natural or synthetic amino acid sequence, the sequence of which totally or partially comprises an abovementioned amino acid sequence, for example the variants and the analogs.

A person skilled in the art can obtain an amino acid sequence in accordance with the invention by means of processes based on recombinant DNA, for instance those described in the manual *Molecular Cloning—A Laboratory Manual* (2nd edition), Sambrook et al., 1989, Vol. I-III, Coldspring Harbor Laboratory, Coldspring Harbor Press, NY, (Sambrook).

According to another embodiment, an amino acid sequence suitable for the invention can also be an amino acid sequence as previously defined, fused with another amino acid sequence, a hydrophilic or hydrophobic targeting agent, a bioconversion precursor, or a luminescent, radioactive or colorimetric labeling agent, or alternatively an antibody labeling agent.

In a nonlimiting manner, mention may be made, as examples of compounds which can be coupled to an amino acid sequence in accordance with the invention, of fluorescent proteins such as Green Fluorescent Protein, fluorescent chemical compounds, such as rhodamine, fluorescein, or Texas Red®, phosphorescent compounds, radioactive elements, such as $^{3}H$, $^{14}C$, $^{35}S$, $^{121}I$ or $^{125}I$, or colorimetric labeling agents such as chromogenic substrates sensitive to the action of galactosidase, of peroxidase, of chloramphenicol acetyltransferase, of luciferase or of alkaline phosphatase, or an antibody labeling agent, such as His-Tag.

Depending on the nature of the compounds that may be coupled with an amino acid sequence of the invention, the coupling may be performed via chemical processes, in particular by means of reactive chemical functions, or via molecular biology processes known to those skilled in the art.

According to one embodiment, the present invention also relates to nucleic acid sequences encoding an amino acid sequence of the invention and the implementation thereof in the various uses and processes of the invention.

Thus, the present invention also relates to a nucleic acid sequence, in particular a deoxyribonucleic acid sequence or a ribonucleic acid sequence, represented by SEQ ID No.: 1, or an analog or fragment thereof.

Advantageously, an amino acid sequence of the invention can be encoded by a nucleic acid sequence chosen from a sequence represented by SEQ ID No.: 1, SEQ ID No.: 2, SEQ ID No.: 3, SEQ ID No.: 4, SEQ ID No.: 5, SEQ ID No.: 6 or SEQ ID No.: 7, or an analog or fragment thereof.

Preferably, a nucleic acid sequence of the invention may be represented by a sequence chosen from SEQ ID No.: 2, SEQ ID No.: 3, SEQ ID No.: 4, SEQ ID No.: 5, SEQ ID No.: 6 or SEQ ID No.: 7, or an analog or fragment thereof.

A nucleic acid sequence of the invention can be of any possible origin, namely animal, in particular mammalian and even more particularly human, or plant, or from microorganisms, such as, for example, viruses, phages or bacteria, inter alia, or else from fungi, without any preconception as to whether or not they are naturally present in said organism of origin.

According to one embodiment, the invention also relates to the isolated and purified nucleic acid sequences encoding an amino acid sequence under consideration according to the invention, and also to the analogs and fragments thereof.

A nucleic acid sequence in accordance with the invention can comprise a sense, antisense or interfering sequence corresponding to a sequence encoding a polypeptide in accordance with the invention.

A subject of the invention is also nucleic acid sequences, in particular ribonucleic acid sequences or deoxyribonucleic acid sequences, comprising a sense or antisense, in particular small interfering RNA (siRNA), sequence corresponding at least to a sequence encoding a protein or a peptide of the invention or a nucleic acid sequence of the invention, or a fragment or analog thereof.

The invention also relates to RNA or DNA aptamer sequences capable of modulating the activity of the enzyme.

The invention also relates to monoclonal or polyclonal antibodies obtained via standard techniques, or, preferably, recombinant human antibodies selected against IDE via phage display techniques, such as those proposed by the company AbD Serotec, or "Nanobodies", as proposed by the company Ablynx.

Skin Desquamation and Dandruff Conditions

As indicated previously, a scalp presenting excessive dryness or excessive secretion of sebum may manifest a dandruff condition, which, depending on the case, may be characterized by the presence of dry or greasy dandruff flakes, or even pruritus and/or inflammation of the epidermis.

Dry dandruff conditions reflect a xerosis of the scalp, which may be combined with excessively rapid renewal of its stratum corneum. Dry dandruff flakes are generally small and white or gray, and are spread over the scalp and on clothing, giving rise to an unesthetic visual effect. The itching associated with dryness of the scalp may lead to erythema, pruritus or even inflammation.

Greasy dandruff conditions are one of the forms of seborrheic dermatitis. Individuals suffering therefrom have an erythemal scalp covered by large, greasy yellow squamae that accumulate to form packets. They have a pruriginous scalp, and often have burning sensations on the affected areas. Greasy dandruff conditions of the scalp are manifested, and are amplified, during excessive secretion of sebum in the scalp epidermis. Greasy dandruff conditions in their severe forms may be forms of seborrheic dermatitis.

These phenomena may be amplified by the presence of pathogenic microorganisms, especially *Malassezia* sp. These microorganisms having the property of releasing fatty acids from the sebum may impair the barrier function of the epidermis and give rise to inflammation.

During attacks of dandruff of the scalp, the skin barrier is imbalanced, its integrity and its hydration are impaired and its ecoflora perturbed. The skin of the scalp is irritated and pruriginous, fragile, less hydrated, and sensitive to infection.

The use of an amino acid sequence or of a nucleic acid sequence of the invention or of a modulatory agent of the invention leads to re-establishment of the moisturization and the ecoflora and to a reduction of pruritus of the scalp. This decrease is reflected by a reduction in the phases of scratching the scalp and of impairment of the barrier function resulting therefrom. The efficacy of the treatment is thus markedly improved and is developed much more quickly. The skin is then less irritated and less pruriginous and the presence of dandruff is reduced, or even eliminated.

The uses, processes and compositions according to the invention thus prove to be most particularly effective:

for preventing and/or treating disorders, especially esthetic disorders, of the scalp associated with excessive dryness, or even xerosis, for preventing and/or treating disorders, especially esthetic disorders, of the scalp associated with excessive excretion and/or secretion of sebum, for preventing and/or treating dandruff conditions, whether they are dry or greasy, of the scalp, for improving and/or re-establishing the antimicrobial defences of a dry or greasy scalp, for improving the comfort of the skin and the scalp, for improving the hygiene and/or care of the scalp, for giving the scalp a feeling of well-being, for preserving and/or reinforcing the integrity of the barrier functions of the skin of the scalp, for maintaining and/or restoring the biomechanical properties of the scalp, for re-establishing a balanced ecoflora of the scalp, for preventing and/or treating pruritus and/or seborrheic dermatitis associated with dandruff conditions of the scalp, and/or for preventing and/or treating the inflammations associated with dandruff conditions of the scalp.

Advantageously, the invention may be performed to prevent and/or treat a disorder of the barrier properties of the scalp.

As explained hereinbelow, the dandruff conditions of the scalp that are under consideration in the invention are other than psoriasis of the scalp.

More generally, the present invention may be performed with regard to desquamation, especially abnormal or irregular desquamation, of the skin, for the purpose of maintaining or restoring the homeostasis of the skin, and in particular the barrier properties of the epidermis. Thus, the present invention may also be performed to prevent and/or treat a disorder of the barrier properties of the scalp.

Depending on the severity of the deregulation of desquamation, the subsequent skin desquamation disorders may fall either within the cosmetic field or within the therapeutic field. It falls to the general knowledge, and the usual practice, of a person skilled in the art to distinguish the skin desquamation disorders as a function of the field thereby concerned.

Abnormal or irregular desquamation may be reflected by thickening or thinning of the stratum corneum, occasionally accompanied by disorders of the barrier function of the skin. In esthetic terms, skin presenting abnormal desquamation may be skin showing signs of dryness or cutaneous xerosis, roughness, dandruff or squamae.

When the abnormal desquamation is greatly aggravated, the condition of the skin may fall within the therapeutic field and present atopic dermatitis, ichthyosis or psoriasis.

Biomarker

A biomarker of the invention advantageously makes it possible to characterize the desquamation, especially abnormal desquamation, of the skin, and preferably a dandruff condition of the scalp.

According to one embodiment of the invention, an increase or decrease in the activity, expression or maturation of a biomarker of the invention may be indicative of abnormal or irregular desquamation of the skin, and preferably of a dandruff condition of the scalp.

According to a preferred embodiment, an increase in the activity, expression or maturation of a biomarker of the invention may be indicative of a dandruff condition of the scalp.

A biomarker may be used to characterize the efficacy of a cosmetic skin treatment, especially with regard to abnormal or irregular desquamation of the skin. In particular, the cosmetic treatment whose efficacy is characterized may be a treatment of a dandruff condition of the scalp.

An increase or decrease in the activity, expression or maturation of the biomarker may be indicative of an effective cosmetic treatment, and especially for exerting a beneficial effect on abnormal or irregular desquamation of the skin, in particular with regard to a dandruff condition of the scalp.

A decrease or increase in the activity, expression or maturation of the biomarker may be determined by comparison with a reference measurement obtained according to any method known to those skilled in the art.

A "reference measurement" from the viewpoint of a given parameter is a qualitative or quantitative measurement of this parameter carried out under "control" or "normal" conditions, for example determined in a reference sample, or determined in a sample in the absence of a treatment presumed to have an effect on the parameter.

A sample that is suitable for use in the invention may be a sample of isolated skin taken from an individual or from an in vitro model of reconstructed skin.

For example, a reference measurement for an amino acid sequence or a nucleic acid sequence in accordance with the invention may be a quantitative or qualitative value relative to the expression, maturation or activity of said sequences, determined in a sample of physiologically healthy skin presenting normal or regular desquamation, or determined in a sample of skin, in particular presenting a skin desquamation disorder, before a cosmetic treatment.

Preferably, a reference measurement is a statistical measurement, i.e. a measurement having been repeated on various samples so as to obtain a mean.

The reference measurement can be carried out in parallel with or sequentially to the test measurement.

It can also be a "historical" measurement, i.e. one carried out prior to the test measurement, and stored, for example in a database, for the purpose of subsequent use.

A comparison of the test measurement with a reference measurement, and observation of a deviation or an absence of deviation between the two measurements, makes it possible to extract information regarding the parameter measured, for example the decrease or increase in the expression, in the maturation or in the activity of an amino acid sequence or of a nucleic acid sequence in accordance with the invention.

Such information may subsequently be used to determine the presence of normal or regular desquamation or, in contrast, abnormal or irregular desquamation of a skin.

When a biomarker of the invention used is an amino acid sequence, abnormal or irregular desquamation of the skin may be reflected by a deviation of the expression of this sequence by a factor of at least 1.2, preferably of at least 1.5 and more preferably of at least twice the normal reference value.

The invention may also be performed on a sample of skin, taken from an epidermal cell model, or from a reconstructed isolated skin in order to describe the state thereof.

According to yet another aspect, a biomarker of the invention may be used for selecting, from among a set of active agents for preventing and/or treating a skin desquamation disorder, an active agent presumed to exert the maximum beneficial effect with regard to said disorder.

The set of active agents in which a selection of a use of the invention may be made may be the set of active agents conventionally used for treating a desquamation disorder. More particularly, a biomarker of the invention may be used for selecting an active agent that is the most suited to the treatment of an individual presenting a dandruff condition of the scalp. In such a case, the active agents that will be considered are those usually used for the treatment of dandruff conditions.

Thus, a biomarker of the invention may advantageously be used for establishing a counseling service personalized for an individual presenting a skin desquamation disorder, and in particular presenting a dandruff condition of the scalp.

Depending on the degree of deviation of the biomarker relative to a normal reference, the counselor may make a choice toward the most suited product so as to obtain the best correction of the biomarker relative to the normal, while at the same time reducing the risk of occurrence of adverse or side effects that might prove to be detrimental to good compliance with the treatment.

According to another aspect, a biomarker of the invention may also be used in a process for selecting and constituting a group of individuals for performing clinical trials dedicated to evaluating the efficacy of a product presumed to be active with regard to abnormal desquamation of the skin, and preferably a dandruff condition of the scalp.

Advantageously, to obtain significant results after a clinical trial, a biomarker of the invention may be used in order to define homogeneous groups of individuals having the same degree of deviation of the biomarker relative to a reference value.

According to one embodiment, the invention relates to a process, in particular an in vitro or ex vivo process, for characterizing a desquamation state of the skin.

A process of the invention advantageously makes it possible to characterize a skin desquamation disorder resulting from abnormal or irregular desquamation, and more particularly a dandruff condition of the scalp.

According to another embodiment, the invention relates to a cosmetic, or nontherapeutic, process, in particular an in vitro or ex vivo process, for characterizing the efficacy of a cosmetic skin treatment, and preferably a treatment of abnormal skin desquamation, and preferably a dandruff condition of the scalp in an individual in need thereof, comprising at least the steps consisting in:

a) performing, before implementing the cosmetic treatment, in a first isolated skin sample, and preferably an isolated scalp sample, taken from said individual, at least a first qualitative or quantitative measurement of the expression, maturation or activity of at least one amino acid sequence of the invention or of at least one nucleic acid sequence of the invention, b) performing, after implementing the cosmetic treatment, in a second isolated skin sample, and preferably an isolated scalp sample, taken from said individual, at least a second qualitative or quantitative measurement of the expression, maturation or activity of said amino acid sequence of the invention or of said nucleic acid sequence of the invention, and c) comparing the first and second measurements, in particular in order to deduce therefrom information relating to at least one effect of the implementation of the cosmetic treatment.

It goes without saying that the measurements carried out in steps a) and b) must be comparable to each other, and therefore relate to the same parameter.

Preferably, a process of the invention makes it possible to demonstrate an effect of a cosmetic treatment capable of normalizing abnormal or irregular desquamation of the skin, and in particular a dandruff condition of the scalp.

More preferably, a process of the invention makes it possible to characterize the efficacy of a cosmetic treatment, and in particular a treatment of a dandruff condition of the scalp.

A qualitative or quantitative measurement of an expression, maturation or activity of a nucleic acid sequence of the invention may be determined by any method known to those skilled in the art.

By way of example of methods suitable for the invention, mention may be made of the quantitative polymerase chain reaction (Q-PCR) or nonquantitative polymerase chain reaction (PCR), in the presence or absence of reverse transcriptase (RT-PCR or Q-RT-PCR), Northern blotting, the ribonuclease protection assay method, methods with DNA chips, methods with transcriptome chips, methods with oligonucleotide chips, and in situ hybridization methods.

By way of example of agents suitable for detecting a nucleic acid sequence of the invention, and in particular an mRNA sequence, mention may be made of labeled nucleic acid probes which can hybridize to a nucleic acid sequence of the invention.

Such a nucleic acid probe can be easily obtained by any method known to those skilled in the art.

Thus, the nucleic acid sequences in accordance with the invention can be used to prepare sense and/or antisense oligonucleotide primers which hybridize, under high stringency conditions, to at least one of the sequences SEQ ID No.: 1, SEQ ID No.: 2, SEQ ID No.: 3, SEQ ID No.: 4, SEQ ID No.: 5, SEQ ID No.: 6, or SEQ ID No.: 7, or an analog or fragment thereof.

The expression of a nucleic acid sequence can also be determined, indirectly, by determining the expression of the amino acid sequence encoded by said sequence, by means of any technique known in the field, such as Western blotting, ELISA, the BRADFORD method or the LOWRY method, or as indicated hereinafter 2D electrophoresis.

A qualitative or quantitative measurement of an expression, maturation or activity of an amino acid sequence of the invention may be performed by any method known to those skilled in the art.

By way of methods for detecting the expression, the maturation or the activity of an amino acid sequence, mention may be made of Western blotting, slot blotting, dot blotting, ELISA (Enzyme Linked Immuno-Sorbent Assay) methods of singleplex or multiplex type, proteomic or glycomic methods, 2D difference electrophoresis proteomic analysis, methods for staining polypeptides in a polyacrylamide gel with a silver-based stain, with Coomassie blue or with SYPRO, immunofluorescence methods, UV absorption methods, immunohistochemical methods by conventional, electron or confocal microscopy, FRET (fluorescence resonance energy transfer) methods, TR-FRET (time resolved FRET) methods, FLIM (fluorescence lifetime imaging microscopy) methods, FSPIM (fluorescence spectral imaging microscopy) methods, FRAP (fluorescence recovery after photobleaching) methods, reporter gene methods, AFM (atomic force microscopy) methods, surface plasmon resonance methods, microcalorimetry methods, flow cytometry methods, biosensor methods, radioimmunoassay (RIA) methods, isoelectric focusing methods, and enzymatic tests, methods using peptide chips, sugar chips, antibody chips, mass spectrometry methods, and spectrometry methods of SELDI-TOF type (Ciphergen), or quantification methods via mass spectrometry of MRM type (multiple reaction monitoring).

More generally, immunoenzymatic assay methods using protein solutions, which are more quantitative and sensitive, can in particular be used. These ELISA-type methods combine pairings of target-antigen-specific capture antibody and detection antibody. Commercial antibodies or specifically developed polyclonal, monoclonal or recombinant antibodies can be used. High capacity multiplex ELISA techniques can also be used. Mention may thus be made of the multiplex approach of the type such as antibodies on Luminex beads (for example Bioplex from Bio-Rad), the singleplex or multiplex approach by chemiluminescence from the company MesoScale Discovery (MSD), or of the type such as antibodies on a flat surface (antibody arrays) (for example the approach proposed by the company MesoScale Discovery).

In particular, it may be advantageous to detect the expression of an amino acid sequence of the invention by means of an antibody, where appropriate in labeled form. Such an antibody can be labeled by means of a substance that is directly detectable or detectable by reaction with another reagent.

The term "antibody" is intended to denote, generally, monoclonal or polyclonal antibodies, and also immunoglobulin fragments capable of binding an antigen and which can be produced by any genetic engineering technique known to those skilled in the art or by enzymatic or chemical cleavage of an intact antibody.

An antibody that may be used as a tool for evaluating the condition of an epidermis may be obtained via any process known to those skilled in the art, as described in *Antibodies: A Laboratory Manual*, Cold Spring Harbor Laboratory Press, Cold Spring Harbor, N.Y. (1990).

According to a preferred embodiment, it may be advantageous to detect the expression of an amino acid sequence of the invention by means of a 2D difference electrophoresis proteomic analysis or via iTRAQ isobaric labeling, or via label-free spectral counting, or of the SILAC type if cell cultures are involved.

Such a method is known to those skilled in the art and can advantageously be carried out as described in the examples hereinafter.

In particular, the term "activity" with regard to an amino acid sequence of the invention means proteolytic activity as indicated previously, or activity for reducing, preventing or treating a skin desquamation disorder, for example as defined previously, and especially a dandruff condition of the scalp.

Such activity may be determined via any method known to those skilled in the art, for instance by evaluation of proteolytic activity on a common substrate of IDE such as insulin, glucagon or the β-amyloid protein.

Preferably, the determination of a state of the skin or the characterization of the efficacy of a cosmetic treatment for the skin can be carried out by measuring the variation in the expression of an amino acid sequence of the invention, and which is preferably represented by a sequence chosen from SEQ ID No.: 8 to SEQ ID No.: 14, or an analog or fragment thereof.

The processes of the invention are particularly advantageous since the implementation thereof does not require recourse to an invasive technique. A sample of epidermis can thus be obtained by "stripping" techniques and directly analyzed by a conventional analysis technique known to those skilled in the art.

These strippings are adhesive surfaces applied to the surface of the epidermis, such as Blenderm® from 3M, D' squam (commercial adhesive from CuDERM), cyanoacrylate glue or the varnish "stripping" method or corneodiscs. By virtue of these strippings, the adherent corneocytes and the content of their intercellular spaces can be sampled and subsequently subjected to extraction in order to access the protein content.

The taking of a sample suitable for a process of the invention can also be carried out more directly by "washing" the skin surface, by means, for example, of accessories of the vane turbine type or of the spiral cell type as described in the patent FR 2 667 778 combined with a fluid circuit, or simply by addition/sampling of a drop of buffer at the surface of the skin.

As a guide, other sampling methods suitable for implementing the invention may be mentioned, such as methods by scraping the upper part of the stratum corneum by means of a twin blade system. This technique makes it possible to collect squamae which can then be directly analyzed by various techniques in order to determine the mineral, amino acid or lipid contents.

Advantageously, one of the markers of the invention may be used for the purposes of more efficient and more rigorous preclinical selection, of individuals, with a view to evaluating the efficacy of a cosmetic treatment or of a cosmetic active agent for skincare, and especially scalp care.

Similarly, a biomarker of the invention may advantageously be used as previously indicated for evaluating the efficacy of an active agent, in vitro, ex vivo or in vivo.

Similarly, a biomarker of the invention may be used for establishing personalized advice for a cosmetic treatment for an individual according to said individual's skin biomarker expression profile.

Screening

According to one of its aspects, the present invention relates to the use of a biomarker of the invention, for the screening or in a process of screening, in particular in vitro or ex vivo, of active agents or physical treatments for skincare.

The screened active agents or physical treatments may especially be used for preventing and/or treating abnormal or irregular desquamation of the skin, and preferably for preventing and/or treating a dandruff condition of the scalp.

A use or a screening process of the invention may comprise the comparison of a measurement of the activity, expression or maturation of an amino acid sequence or of a nucleic acid sequence in accordance with the invention, with a reference measurement.

A reference measurement may be as previously defined.

In particular, a reference measurement may be a quantitative or qualitative value relating to the expression, maturation or activity of said sequences, determined in a sample in the absence of active agent or of physical treatment tested.

Thus, a reference measurement may be obtained by repeating the steps of a process of the invention, and especially steps a), b) and c) of a process of the invention as previously defined, in the absence of active agents, or physical treatments to be tested.

A comparison of the test measurement with a reference measurement, and observation of a deviation or of an absence of deviation between the two measurements, makes it possible to extract information with regard to the effect of the active agent or of the physical treatment tested.

The qualitative or quantitative determination of the expression, of the maturation or of the activity of an amino acid sequence or of a nucleic acid sequence of the invention can be carried out by any method known to those skilled in the art, and in particular as previously described.

According to one embodiment, the screening for an active agent or a physical treatment capable of modulating the activity of an amino acid sequence of the invention can be carried out by measuring the activity or the expression of a target molecule belonging to the signaling or metabolic pathways in which said amino acid sequence may be involved, such as, for example, a reporter gene system.

According to one embodiment, a process of the invention may be performed in an acellular system, i.e. in a system which does not comprise cells but which reproduces cell functions, or in an isolated cell sample.

A process in accordance with the invention may be performed on an isolated cell sample, an acellular sample, on an isolated amino acid sequence or on an isolated nucleic acid sequence of the invention. These samples or sequences may be obtained by skin biopsy, from cells in culture, especially from an epidermal model, or from a noninvasive skin surface sampling, especially by adhesive ("tape stripping"), of the stratum corneum or by simple washing, as described previously, or alternatively, as regards sequences, via synthesis.

The use of these samples or sequences for the screening of active agents or of a physical treatment in accordance with the invention falls within the general knowledge of a person skilled in the art in this field.

Advantageously, by way of a cell sample suitable for the invention, mention may be made of a sample of keratinocytes or any other skin cell type expressing an amino acid sequence of the invention.

Preferably, the screening for an active agent or for a physical treatment may be performed by measuring the variation in the expression or activity, in the presence and in the absence of the active agent or of the physical treatment screened, of an amino acid sequence of the invention, and which is preferably represented by a sequence chosen from SEQ ID No.: 8 to SEQ ID No.: 14, or an analog or fragment thereof, and preferably chosen from SEQ ID No.: 9 to SEQ ID No.: 14, or an analog or fragment thereof.

Modulatory Agent

For the purposes of the present invention, the expression "modulatory agent" or "active agent or a physical treatment capable of modulating the expression, the maturation or the activity of an amino acid sequence or of a nucleic acid sequence in accordance with the invention" means any compound or physical phenomenon capable of acting, directly or indirectly, on at least one amino acid sequence or one nucleic acid sequence in accordance with the invention, or on an element of an intracellular or extracellular signaling pathway, or of a metabolic pathway, or for regulating transcription and/or translation, involving said amino acid sequence or said nucleic acid sequence.

The modulatory agents or physical treatments that are preferred according to the invention may be compounds or physical treatments that act directly on at least one amino acid sequence of the invention or at least one nucleic acid sequence of the invention in order to modulate their expression, maturation or activity.

For the purposes of the invention, the term "modulating" means, from the viewpoint of a given effect, the action of stimulating or inhibiting this effect.

The active agents or physical treatments derived from a screening according to the invention may be advantageously used for cosmetic purposes, especially with regard to skin desquamation disorders, especially disorders of the barrier properties of the skin, and in particular disorders of the barrier properties of the scalp.

According to a preferred embodiment, a modulatory agent of the invention is an agent for inhibiting the activity, expression or maturation of an amino acid sequence of the invention. Even more preferably, a modulatory agent of the invention is an agent for inhibiting the enzymatic activity of an amino acid sequence of the invention.

A modulatory agent which inhibits the enzymatic activity of an amino acid sequence of the invention may be chosen from ATP, ADP, N-ethylmaleimide, 1,10-phenanthroline, bacitracin, insulin, hGH, PMSF, fatty acids such as palmitic acid, linoleic acid, palmitoyl-CoA, linoleoyl-CoA, metal ions such as $Mg^{2+}$, $Mn^{2+}$, $Zn^{2+}$, $Li^+$, dynorphin, ubiquitin, metal-chelating agents, especially Zn-chelating agents such as EDTA, hydroxamate peptides having the following general formula:

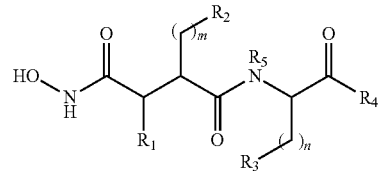

in which $R_1$, $R_2$, $R_3$, $R_4$, $R_5$ and $R_6$ are independent of each other, and in which:

$R_1$ is H, OH, O—$(C_1-C_6)$alkyl or $(C_1-C_6)$alkyl, $R_2$ is a $(C_5-C_{10})$aryl, a $(C_5-C_{10})$heteroaryl comprising at least one N, O or S, a phenyl, a 1-naphthyl, a 2-naphthyl, where appropriate substituted with a halogen, especially Cl or F, a $(C_1-C_6)$alkyl or an O—$(C_1-C_6)$ alkyl, a nitrile, a CN, a $(C_5-C_{10})$aryl, a $(C_5-C_{10})$heteroaryl comprising at least one N, O or S, or a $CO_2H$, $R_3$ is NHC(=NH)$NH_2$, $NH_2$, NHC(O)$(C_1-C_6)$alkyl or NHC(O)$(C_5-C_{10})$aryl, $R_4$ is $[C(=O)CH(CH_2)_oR_7NH]_pH$ or $[C(=O)CH(CH_2)_o R_7NH]pC(=O)Me$ with $R_7$ being 4-hydroxyphenyl, $CO_2H$, 3-indolyl, or a phenyl, o ranging from 0 to 3 and p ranging from 0 to 2, $R_5$ is H or Me, $R_6$ is H or Me, m ranges from 0 to 3 and n ranges from 0 to 3.

The hydroxamate peptides that are suitable for use in the invention are more particularly described in WO 2008/156 701.

Preferably, a hydroxamate peptide that is suitable for use in the invention may be a compound of the preceding general formula (I), in which $R_2$ is a 2-naphthyl, and $R_3$ is NHC(=NH)$NH_2$, and $R_1$, $R_4$, $R_5$ and $R_6$ are as defined previously.

Even more preferably, $R_2$ may be an aryl, a heteroaryl, a substituted aryl, a substituted heteroaryl, a halo-substituted aryl such as a 2-fluorophenyl, a 3-fluorophenyl, a 4-fluorophenyl, a halo-substituted heteroaryl, an alkyl- or aryl-substituted aryl, an alkyl- or aryl-substituted heteroaryl, such as a 2-tert-butyl, 3-tert-butyl, 4-tert-butyl, phenyl, a 1-naphthyl, 2-naphthyl, 2-benzothiophene, -trans-CH=CH-phenyl, 2-phenyl, 3-phenyl or 4-phenyl.

Even more particularly, a hydroxamate peptide that is suitable for use in the invention may be chosen from:

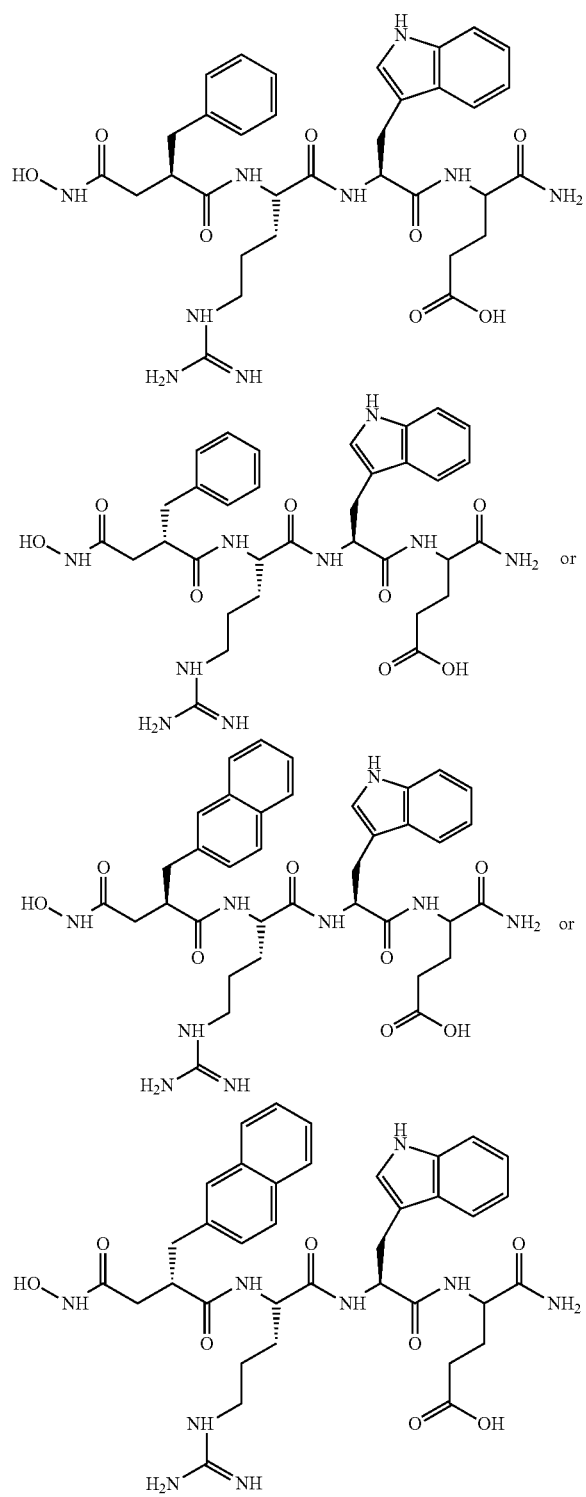

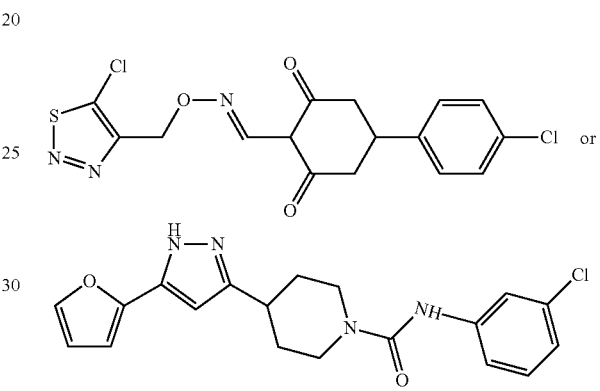

These compounds are especially described in Cabrol et al. (PLoSOne, 2009).

Among the activators of the enzymatic activity of IDE, mention may also be made of nucleoside phosphates, peptide fragments of IDE, or antibodies that activate the enzyme.

As modulatory agents that may be screened according to a use or a process in accordance with the invention, mention may also be made of antibodies, derived especially from banks of recombinant antibodies, for example from the company Antibodies By Design, and which are capable of blocking the active site or exosite of the enzyme, or of activating the enzyme, for example via the allosteric effect, or interfering RNAs, such as siRNA, miRNA or shRNA, or RNA or DNA aptamers.

Compositions

The present invention also relates to compositions, in particular cosmetic compositions, comprising, in a physiologically or cosmetically acceptable medium, an effective amount of at least one amino acid sequence of the invention, or of at least one nucleic acid sequence of the invention, or of at least one active agent capable of modulating the activity, expression or maturation of said amino acid sequence or of said nucleic acid sequence.

More particularly, the invention relates to a cosmetic composition comprising a peptide represented by an amino acid sequence chosen from SEQ ID No.: 9 to SEQ ID No.: 14, or an analog or fragment thereof, or a nucleic acid sequence encoding such a peptide.

For the purposes of the present invention, the expression "physiologically acceptable medium" is intended to denote a medium that is suitable for the administration of a com- Besides the inhibitory agents mentioned previously, mention may also be made, as IDE inhibitors, of compounds of nucleoside phosphate type or peptide fragments of IDE, and also interfering RNAs, DNA or RNA aptamers or antibodies that block the active site or the exosite of the enzyme.

According to one embodiment of the invention, a modulatory agent of the invention, especially an agent that inhibits the activity, expression or maturation of an amino acid sequence of the invention, may be advantageously used for preventing and/or treating a dandruff condition of the scalp. More preferably, the invention relates to the use of a modulatory agent that inhibits the enzymatic activity of an amino acid sequence of the invention for preventing and/or treating a dandruff condition of the scalp.

According to another aspect, the invention also relates to modulatory agents of the invention chosen from activators of the activity, expression or maturation of an amino acid sequence of the invention and especially activators of the enzymatic activity of an amino acid sequence of the invention.

According to one embodiment, a modulatory agent that activates enzymatic activity may be chosen from suramin, somatostatin, bradykinin, β-endorphin, dynorphin, ATP, iPPP, ADP, AMP, fatty acids, especially such as docosahexaenoic acid, and the compounds having the following formulae:

position topically to the skin, the scalp or the lips, or orally or parenterally, such as intradermally or subcutaneously.

A composition of the invention may contain adjuvants that are common in the field under consideration, such as hydrophilic or lipophilic gelling agents, hydrophilic or lipophilic additives, preserving agents, antioxidants, solvents, fragrances, fillers, screening agents, odor absorbers and colorants.

The amounts of the various constituents of the compositions according to the invention are those conventionally used in the fields under consideration.

The amount of amino acid sequence or nucleic acid sequence of the invention or of active agent in accordance with the invention, contained in a composition of the invention, also referred to as "effective amount", depends of course on the nature of the active agent and on the desired effect and can therefore vary to a large extent.

To give an order of magnitude, a composition can contain an amino acid sequence or a nucleic acid sequence or an active agent in accordance with the invention in an amount representing from 0.00001% to 50% of the total weight of the composition, in particular in an amount representing from 0.001% to 10% of the total weight of the composition and more particularly in an amount representing from 0.1% to 1% of the total weight of the composition.

According to another embodiment, a cosmetic composition of the invention may also comprise at least one additional cosmetic and/or therapeutic active agent.

Additional Active Agents

As examples of additional active agents that may be used in the context of the present invention, mention may be made of cosmetic oils, such as silicone oils, plant oils of triglyceride type, hydrocarbon-based oils, such as Parleam oil, and esters of fatty acids and of fatty alcohols.

It may also be possible to use other active agents for improving the state of the skin and/or of its appendages, such as moisturizing or humidifying active agents or active agents for improving the natural lipid barrier, such as ceramides, cholesterol sulfates and/or fatty acids, and mixtures thereof.

It may also be possible to use enzymes which have an activity on the skin and/or its appendages, such as proteases, lipases, glucosidases, amidases, cerebrosidases and/or melanases, and mixtures thereof.

Other examples of active agents that are suitable for the implementation of the present invention include: analgesic active agents, anti-yeast active agents, antibacterial active agents, antiparasitic active agents, antifungal active agents, antiviral active agents, steroidal antiinflammatory active agents, anesthetic active agents, antipruritic active agents, keratolytic active agents, free-radical scavenging active agents, antiseborrheic active agents, antidandruff active agents, antiacne active agents, active agents for preventing aging of the skin and/or for improving the state thereof, antidermatitis active agents, antiirritant active agents, immunomodulatory active agents, active agents for treating dry skin, antiperspirant active agents, antpsoriatic active agents, UV-protecting active agents, antihistamine active agents, cicatrizing active agents, self-tanning active agents, antioxidants such as green tea or active fragments thereof, glycerol, laponite, caffeine, aromatic essential oils, dyes, depigmenting active agents, liporegulators, softening, refreshing, deodorizing, desensitizing, bleaching or nourishing active agents, active agents for reducing skin differentiation and/or proliferation and/or pigmentation, and mixtures thereof.

Also, as additional active agents, mention may be made of Tween 20 or of other mild detergents, chelating agents, probiotic agents, Zn-pyrithione or other antifungal agents, ellagic acid, prodesquamating agents and/or peeling agents, anti-pruritus compounds, polyphenols and derivatives thereof, sugars and reducing sugars, antiinflammatory agents, antiperspirants or antisebacic agents, etc.

By way of additional active agents that may be more particularly suitable for use in the invention, mention may also be made of probiotic microorganisms, prebiotic active agents, active agents for promoting the synthesis of skin defense factor, active agents for re-establishing the differentiation/proliferation equilibrium of epidermal cells, in particular such as active agents of retinol or retinol-like type, or moisturizing active agents.

Cosmetic Use

The present invention relates to the cosmetic use of an effective amount of at least one agent that modulates the activity, expression or maturation of said amino acid sequence or of said nucleic acid sequence, and especially a modulatory agent as defined previously, as an active agent for preventing and/or treating abnormal or irregular desquamation of the skin, in particular a disorder of the barrier properties of the scalp, and preferably a dandruff condition of the scalp.

According to a preferred embodiment, a use of the invention may implement a modulatory agent that inhibits the activity, expression or maturation of an amino acid sequence of the invention, and preferably an inhibitor of the enzymatic activity of an amino acid sequence of the invention. Such an agent may be chosen especially from the inhibitors defined previously.

According to another embodiment, a use of the invention may implement a modulatory agent that activates the enzymatic activity of an amino acid sequence of the invention, advantageously chosen from the activators defined previously.

According to another aspect, the present invention relates to a cosmetic or nontherapeutic process for preventing and/or treating abnormal or irregular desquamation of the skin, and in particular a dandruff condition of the scalp, in an individual in need thereof.

A process of the invention may comprise at least one step that consists in administering to said individual at least one composition comprising, as active agent, at least one agent that modulates the activity, expression or maturation of said sequences of the invention, especially as defined above.

Preferably, a modulatory agent under consideration is an agent that inhibits the enzymatic activity of an amino acid sequence of the invention, especially as defined previously.

A process or a use of the invention makes it possible to prevent and/or treat a skin desquamation disorder, especially as defined previously, and preferably a dandruff condition of the scalp.

A process of the use of the invention may make it possible to reduce the number and size of the squamae or dandruff.

Advantageously, a scalp may have its esthetic appearance improved and its barrier function properties restored as a result of the implementation of a use or a process in accordance with the invention.

In general, a process or a use of the invention makes it possible to reinforce the barrier properties of the skin, and in particular of the scalp.

Preferably, a process of the invention may comprise the topical application, to at least one part of the skin of an individual in need thereof, in particular to the scalp, of at least one coat of a topical composition of the invention.

A cosmetic process by topical application according to the invention may advantageously comprise the application of a composition of the invention, in combination, simultaneously, successively or separately over time, with an additional cosmetic or dermatological composition distinct from the composition of the invention and intended for caring for and/or making up the skin, and preferably for caring for the scalp.

According to another preferred embodiment, a cosmetic process of the invention can be implemented orally, in particular by administration of at least one food or dietetic composition for cosmetic purposes.

According to another preferred embodiment, a cosmetic process of the invention may be implemented parenterally. The parenteral implementation of a cosmetic process of the invention is performed to the exclusion of any surgical intervention and is merely aimed at performing a surface treatment of the skin for esthetic purposes.

Thus, a cosmetic process of the invention implemented parenterally is carried out by any injection technique or device suitable for an intraepidermal and/or intradermal and/or subcutaneous injection.

Such an administration can be carried out, for example, by mesotherapy.

A cosmetic process implemented parenterally therefore results only in a superficial penetration of the skin and is therefore outside any medical or therapeutic context.

It is alternatively possible, parenterally, to favor administration using a systemic patch.

A cosmetic process according to the invention can be carried out daily, for example at the rate of a single administration per day or of an administration split up into two or three times per day, for example once in the morning and once in the evening.

A cosmetic process according to the invention may be implemented over a time period ranging from one week to several weeks, or even several months, this period moreover possibly being repeated after periods without treatment, for several months or even several years.

By way of example of a cosmetic process according to the invention, it is possible to envision administration of a composition of the invention, for example, at a rate of 1, 2 or 3 times per day, or more, and generally over an extended period of at least 4 weeks, or even 4 to 15 weeks, with, where appropriate, one or more periods of stoppage.

Reconstructed Skin

According to another aspect, the present invention relates to the use of an effective amount of at least one amino acid sequence of the invention, or of at least one nucleic acid sequence of the invention, or of at least one modulatory agent of the invention, for preparing an isolated reconstructed skin.

There is a great advantage in developing organotypic models that are as close as possible to in vivo conditions for evaluating the safety and efficacy of active agents and formulae for cosmetic and dermatological applications.

The use of at least one amino acid sequence of the invention, or of at least one nucleic acid sequence of the invention, or of at least one modulatory agent of the invention, in a culture medium, is capable of improving the quality of the models developed.

Also, a use of the invention may make it possible to obtain a model of isolated reconstructed skin that reproduces desquamation of the skin. In particular, the use of an activating modulatory agent, as defined previously, may be considered for the preparation of a skin model that reproduces desquamation, and preferably that reproduces a dandruff condition.

According to another aspect, the present invention relates to a process for preparing an isolated multistratified epithelial cell model, and preferably an isolated reconstructed skin, comprising at least the step of bringing at least an effective amount of at least one amino acid sequence, or of at least one nucleic acid sequence, or of at least one modulatory agent in accordance with the invention, into contact with cells capable of generating an isolated reconstructed skin, and in particular keratinocytes.

A reconstructed skin model can comprise various cell types, such as keratinocytes, fibroblasts, Langerhans cells and melanocytes. The cells of fibroblast type can optionally be irradiated.

Advantageously, a model of reconstructed skin of the invention may be used as a model of a scalp. A model of isolated reconstructed scalp of the invention may advantageously be used for the purposes of screening novel active agents that are suitable for scalp care, and more particularly novel antidandruff active agents.

Such models and the preparation thereof are known to those skilled in the art.

According to yet another aspect, the present invention also relates to a process for preparing a multistratified epithelial cell model, preferably a reconstructed skin model, comprising at least one step of culturing cells of at least one cell type of said model, said cells having been genetically modified so as to suppress or increase the expression of an amino acid sequence or of a nucleic acid sequence of the invention.

The production of cells genetically modified so as to suppress the expression of an amino acid sequence or of a nucleic acid sequence of the invention, which cells are referred to as "knock-out", can be carried out by any method known to those skilled in the art.

By way of example, such cells can be obtained by transfection and homologous recombination of a nucleic acid fragment which inserts into or takes the place of the gene expressing the amino acid sequence of which the expression is to be suppressed.

Likewise, it may be possible to suppress the expression of a given gene by transfection into the cell of a nucleic acid sequence encoding an interfering RNA specific for the mRNA derived from the gene of which the expression is to be suppressed.

The production of cells genetically modified so as to increase the expression of an amino acid sequence or of a nucleic acid sequence of the invention may be performed via any method known to those skilled in the art.

By way of example, such cells may be obtained by transfection of a plasmid comprising a gene encoding an amino acid sequence of the invention under the control of a promoter. The promoter used may enable the inducible or constitutive or tissue-specific expression of the gene.

Also, it is possible to use various transfection vectors that allow the introduction of the gene to be expressed in the chromosomes of the cells to be transfected.

All these molecular biology techniques making it possible to repress or to increase the expression of a gene are known to those skilled in the art and do not need to be specifically elaborated on.

FIGURES

FIG. 1: shows the magnification of a protein spot, obtained by 2D difference electrophoresis proteomic analysis, identified as being IDE.

Figure 2:
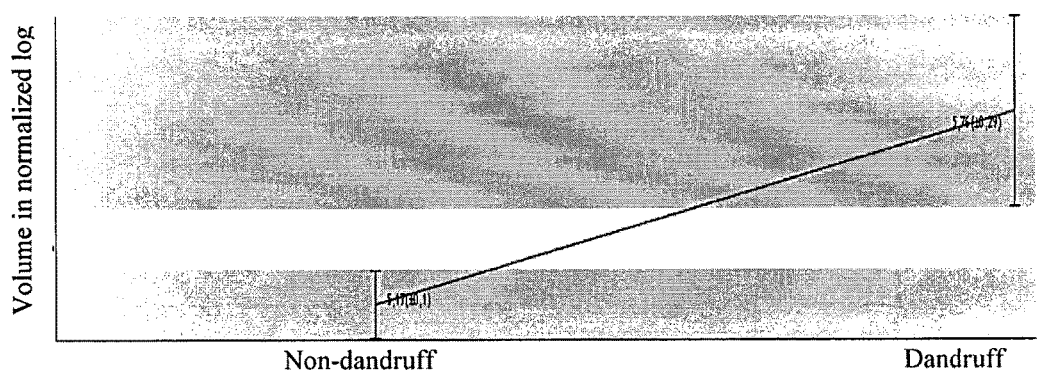

FIG. 2: is a graph of the intensity of the volume of the spots observed in FIG. 1.

Figure 3:
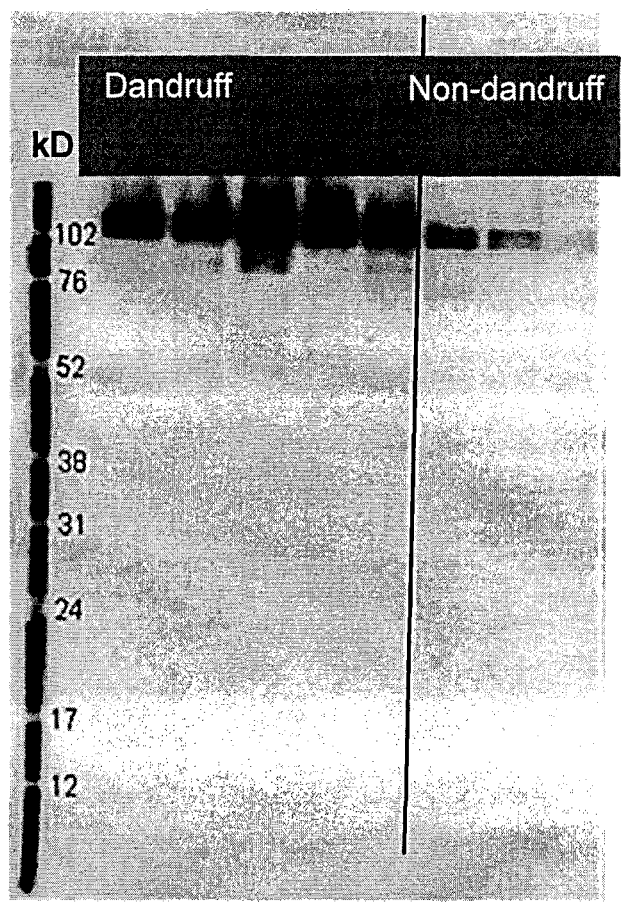

FIG. 3: shows the immunodetection by Western blotting of IDE.

Figure 4:
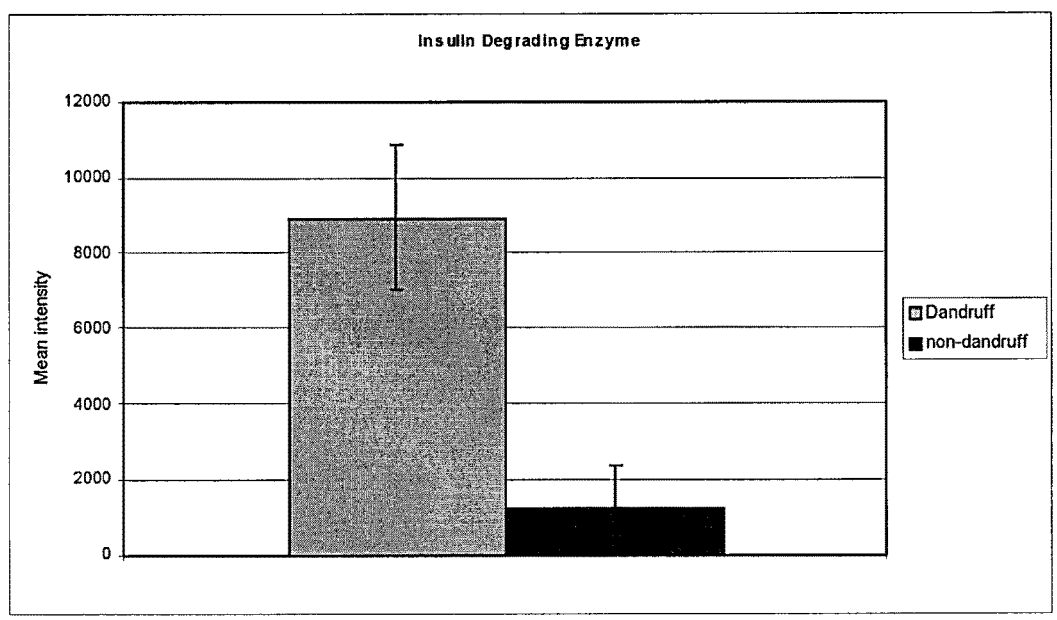

FIG. 4: shows the mean intensity of the bands detected during the Western blotting illustrated by FIG. 3.

For the purposes of the present invention, "one" should be understood, unless otherwise indicated, in the sense of "at least one".

The examples and figures hereinafter are presented by way of illustration and without implied limitation of the invention.

EXAMPLES

Example 1

Expression of IDE in the Scalp

1—Materials and Methods

A 2D difference electrophoresis proteomic analysis performed using noninvasive samples of dandruff-free and dandruff-bearing scalps was performed.

The study is performed on 6 dandruff-free volunteers (adherent dandruff grade from 0 to 0.25) and 6 dandruff-bearing volunteers (adherent dandruff grade from 3.25 to 4). The volunteers are 36 to 39 year-old men with short hair. The grading of the dandruff condition of the volunteers is performed by an expert according to the following standard classification which provides a scale of scores of adherent dandruff of between 0 and 5.

The samples are taken by corneodisc (reference GODS 100, CuDerm) on an area of 2 cm. Four saturated corneodiscs are produced for each sample. The soluble proteins are extracted into a native buffer (TBS, 1M NaCl, 1% Triton X100).

After filtration, the proteins are precipitated by addition of acetone. The protein pellet is dissolved in the extraction buffer III (BioRad; Ref.: 163-2104) supplemented with 40 mM of DTT.

For each sample corresponding to a volunteer, two-dimensional electrophoresis is performed along a first dimension by IEF separation pH 3-11 on an 11 cm strip (GE-Healthcare) and along a second dimension on a 10.5-14% Criterion gradient gel (Bio-Rad) according to the suppliers' recommendations.

After staining the gels with SyproRuby (reference S4942, Invitrogen) used according to the supplier's protocol, an image analysis is performed with the Progenesis™ software after image acquisition according to the following parameters: Excitation: 460/80; Emission: 620/30; Resolution 50 μm; Exposure 3 s; Flat field: 1 s; Exposure 1.

In a first step, the images are aligned together and the intensities normalized. In a second step, after having defined groups, a statistical analysis is performed with the Progenesis Samespots software (NonLinear Dynamics). A selection of spots is made as a function of the "p value" (less than 0.05), the "fold" (greater than 2, ratio of intensity between the most intense spot of one group and the least intense spot of another group) and the "q value" (greater than 0.8).

The selected spots are then cut out and the proteins are digested with trypsin and analyzed by LC-MS/MS.

The protein databank UniRef100.15.3.9606.homo-sapiens was interrogated to identify the proteins.

2—Results

IDE is identified among the spots selected in favor of an overexpression in the dandruff-bearing group according to the criteria defined previously.

Magnification of this protein spot for each volunteer and the graphical representation of the volume of the spots is given by FIGS. 1 and 2.

These results validate the use of IDE as a biomarker for the skin, in particular for skin desquamation, and more particularly for a dandruff condition of the scalp. IDE may thus be advantageously used for the screening of active agents for the treatment of a dandruff condition of the scalp or for characterizing the efficacy of a cosmetic skin treatment.

Example 2

Confirmation by Western Blotting of the Expression of IDE in the Skin

1—Materials and Methods

The concentration of the samples described previously in example 1 is aligned, and 2 μg are deposited in the wells of a 10-20% Criterion gel (BioRad). The proteins are thus separated by SDS-PAGE electrophoresis. After semidry transfer onto a PVDF membrane according to a standard protocol, the proteins are incubated with a primary antibody directed against the protein of interest, overnight at 4° C. A second incubation is then performed with a secondary antibody (coupled to a peroxidase) directed against the first antibody.

An electrochemiluminescence kit is used for revealing the target proteins.

The image is acquired with Fluor Smax (Biorad) and the bands are quantified using the Quantity-One software (Biorad). A commercial anti-IDE antibody was used at a dilution of 1/5000 (reference AB28560, AbCam).

2- Results

FIG. 3 shows the Western blot image obtained. The mean intensity of the detected bands is represented by the histogram in FIG. 4.

The immunodetection of IDE reveals an overexpression in the dandruff-bearing individuals. This observation confirms the differential identifications observed in example 1.

LITERATURE

Ali et al. (2009). "The insulin degrading enzyme binding domain of varicella-zoster virus (VZV) glycoprotein E is important for cell-to-cell spread and VZV infectivity, while a glycoprotein I binding domain is essential for infection." Virology 386(2): 270-279.

Cabrol et al. (2009). "Small-molecule activators of insulin-degrading enzyme discovered through high-throughput compound screening." PLoS One 4(4): e5274.

Camberos et al. (2001). "ATP inhibits insulin-degrading enzyme activity." Exp. Biol. Med. (Maywood) 226(4): 334-341.

Groves et al. (2003). "Association and haplotype analysis of the insulin-degrading enzyme (IDE) gene, a strong positional and biological candidate for type 2 diabetes susceptibility." Diabetes 52(5): 1300-1305.

Guo et al. (2010). "Molecular Basis for the Recognition and Cleavages of IGF-II, TGF-alpha, and Amylin by Human Insulin-Degrading Enzyme." J. Mol. Biol. 395(2): 430-443.

Kim et al. (2007). "Decreased catalytic activity of the insulin-degrading enzyme in chromosome 10-linked Alzheimer disease families." J. Biol. Chem. 282(11): 7825-7832.

Miners et al. (2009). "Neprilysin and insulin-degrading enzyme levels are increased in Alzheimer disease in relation to disease severity." J. Neuropathol. Exp. Neurol. 68(8): 902-914.

Radulescu et al. (2007). "Immunohistochemical demonstration of the zinc metalloprotease insulin-degrading enzyme in normal and malignant human breast: Correlation with tissue insulin levels." Int. J. Oncol. 30:73-80.

Shearer et al. (1997). "Insulin is degraded extracellularly in wounds by insulin-degrading enzyme (EC 3.4.24.56)." Am. J. Physiol. 273(4 Pt 1): E657-664.

Kyte et al. (1982), J. Mol. Biol., 157: 105.

Mehul et al. (2000) "Identification and Cloning of a New Calmodulin-like Protein from Human Epidermis" J. Biol. Chem. 275(17):12841-12847

Sambrook et al. (1989), Vol. I-III, Coldspring Harbor Laboratory, Coldspring Harbor Press, NY.

"Antibodies: A Laboratory Manual", Cold Spring Harbor Laboratory Press, Cold Spring Harbor, N.Y. (1990).

The invention claimed is:

1. An in vitro or ex vivo process for detecting insulin-degrading enzyme (IDE) in an individual having dandruff of the scalp, comprising:
   a) obtaining an isolated scalp sample from the individual; and
   b) performing, in the isolated sample of the scalp taken from said individual, a quantitative measurement of the expression of an amino acid sequence represented by a sequence consisting of SEQ ID No.: 8, or an analog of said amino acid sequence, said analog having a sequence identity of at least 85% with said amino acid sequence, having a biological activity of the same nature and being detectable by antibodies directed against an amino acid sequence represented by a sequence consisting of SEQ ID No.: 8.

2. An in vitro or ex vivo process for detecting insulin-degrading enzyme (IDE) in an individual having dandruff of the scalp, comprising:
   a) obtaining a first isolated scalp sample from the individual;
   b) performing, before implementing the cosmetic treatment of step c), in a first isolated scalp sample taken from said individual, at least a first quantitative measurement of the expression of at least one amino acid sequence represented by a sequence consisting of SEQ ID No.: 8, or an analog of said amino acid sequence, said analog having a sequence identity of at least 85% with said amino acid sequence, having a biological activity of the same nature and being detectable by antibodies directed against an amino acid sequence represented by sequence consisting of SEQ ID No.: 8,
   c) implementing a cosmetic treatment on the scalp of said individual, and
   d) performing, after implementing the cosmetic treatment of step c), in a second isolated scalp sample taken from said individual, at least a second quantitative measurement of the expression of said amino acid sequence represented by a sequence consisting of SEQ ID No.: 8, or an analog of said amino acid sequence, said analog having a sequence identity of at least 85% with said amino acid sequence, having a biological activity of the same nature and being detectable by antibodies directed against an amino acid sequence represented by a sequence consisting of SEQ ID No.: 8.

* * * * *

UNITED STATES PATENT AND TRADEMARK OFFICE
CERTIFICATE OF CORRECTION

PATENT NO.        : 10,351,838 B2
APPLICATION NO.   : 13/993907
DATED             : July 16, 2019
INVENTOR(S)       : Caroline Delattre et al.

It is certified that error appears in the above-identified patent and that said Letters Patent is hereby corrected as shown below:

On the Title Page

Item (56), OTHER PUBLICATIONS, Line 12, "isulin" should read -- insulin --.

Item (56), OTHER PUBLICATIONS, Line 31, "enxyme" should read -- enzyme --.

Item (56), OTHER PUBLICATIONS, Line 34, "Varicell-Zoster" should read -- Varicella-Zoster --.

Signed and Sealed this
Eighth Day of October, 2019

Andrei Iancu
*Director of the United States Patent and Trademark Office*